United States Patent
Dong et al.

(10) Patent No.: US 8,097,705 B2
(45) Date of Patent: Jan. 17, 2012

(54) METHODS AND COMPOSITIONS FOR TREATING ALLERGIC DISEASES

(75) Inventors: Liqun Dong, San Diego, CA (US); Marc Nasoff, San Diego, CA (US)

(73) Assignee: IRM LLC, Hamilton (BM)

( * ) Notice: Subject to any disclaimer, the term of this patent is extended or adjusted under 35 U.S.C. 154(b) by 423 days.

(21) Appl. No.: 12/160,868

(22) PCT Filed: Jan. 11, 2007

(86) PCT No.: PCT/US2007/060379
§ 371 (c)(1),
(2), (4) Date: Jul. 14, 2008

(87) PCT Pub. No.: WO2007/112146
PCT Pub. Date: Oct. 4, 2007

(65) Prior Publication Data
US 2009/0286312 A1    Nov. 19, 2009

Related U.S. Application Data

(60) Provisional application No. 60/759,625, filed on Jan. 13, 2006.

(51) Int. Cl.
*C07K 16/00*    (2006.01)
*C12P 21/08*    (2006.01)

(52) U.S. Cl. .............. 530/388.22; 530/388.1; 530/387.3
(58) Field of Classification Search ....................... None
See application file for complete search history.

(56) References Cited

U.S. PATENT DOCUMENTS 5,534,254 A * 7/1996 Huston et al. .............. 424/135.1
2005/0249712 A1 11/2005 Leonard et al.

FOREIGN PATENT DOCUMENTS

WO    WO2006/023791 A2    3/2006

OTHER PUBLICATIONS

Ruff-Jamison et al., 1991, J. Biol. Chem. vol. 266: 6607-6613.*
Portolano et al., 1993, J. Immunol. vol. 150: 880-887.*
Limka et al., 2000, Brit. J. Canc. vol. 83: 252-260.*
Soumelis et al., "Human Epithelial Cells Trigger Dendritic Cell Mediated Allergic Inflammation by Producing TSLP", Nature Immunology, Nature Publishing Group, 2002 vol. 3 Issue 7 pp. 673-680.
Soumelis et al., "Human Thymic Stromal Lymphopoietin: A Novel Epithelial Cell-derived Cytokine and a Potential Key Player in the Induction of Allergic Inflammation", Springer Seminar in Immunopathology, 2004 vol. 25 Issue 3-4 pp. 325-333.

* cited by examiner

*Primary Examiner* — Amy Juedes
(74) *Attorney, Agent, or Firm* — Novartis AG; Mei Benni

(57) ABSTRACT

Disclosed in the present invention are antibodies that specifically recognize and antagonize human TSLP receptor, and methods of employing these antibodies to treat or ameliorate diseases or disorder mediated by TSLP signaling.

14 Claims, 8 Drawing Sheets

1D6 hybridoma heavy chain DNA sequence (SEQ ID NO: 13)

ATGGCAGCTGCTCAAAGTGCCCAAGCACAGATCCAGTTGGGACAGTCTGGACCTGAG
CGAAGAAGCCTGGAGAGACAGTCAAGATCTCCTGCAAGGCTTCTGGGTATACCTTCACAACC
TATGGAATGAGCTCGGTGAAACAGGCTCCAGGAAAGGGTTTACAGTGGATCGGCTGGATAAA
TACCTACTCTGGAGTGCCAAGATATGCTGATGACTTCAAGGGACGATTTGCCTTCTCTTTGG
AAACCTCTGCCAGCACTGCCTATCTGCAGATCTACAACCTCAAAAATGAGGACACGGCTACA
TATTTCTGTACAAGAGAAGGATTTATTACTACGGTAGTAGGTGCGGCTGGGAGGTTTGTTTA
TTGGGGCCAAGGGACTCTGGTCACTGTCTCTGCA

1D6 hybridoma light chain DNA sequence (SEQ ID NO: 14)

ATGGAGTCACATACTCAGGTCTTTGTATACATGTTGCTGTGGTTGTCTGGTGTTGAA
GAGACATTGTGATGACCCAGTCTCACAAATTCATGTCCACATCAGTAGGAGACAGGGTCAGC
ATCACCTGCAAGGCCAGTCAGGATGTGGGTACCGCTGTAGCCTGGTATCAACAGAAACCAGG
GCAATCTCCTAAACTACTGATTTACTGGGCATCCACCCGGCACACTGGAGTCCCTGATCGCT
TCACAGGCAGTGGATCTGGGACAGATTTCACTCTCACCCTTAACAATGTGCAGTCTGAAGAC
TTGGCAGATTATTTCTGTCAGCAATATAGCACCTATCCCACGTTCGGTAGTGGGACCAAGCT
GGAGCTGAAACGGGCT

Fig. 4

Variable Regions of Anti-hTSLPR Antibody 1D6.C9

Heavy Chain (VH9), subgroup IIA (SEQ ID NO: 5)

MAAAQSAQAQ*IQLGQSGPELKKPGETVKISCKASGYTFT*TYGMS
signal sequence  FR1                          CDR1

WVKQAPGKGLQWMGWINTYSGVPRYADDFKGRFAFSLETSASTAY
FR2            CDR2              FR3

LQIYNLKNEDTATYFCTREGFITTVVGAAGRFVYWGQGTLVTVSA
                CDR3                FR4

Light Chain (LV3), subgroup I or II (SEQ ID NO: 6)

MESHTQVFVYMLLWLSGVEGDIVMTQSHKFMSTSVGDRVSITC
signal sequence              FR1

KASQDVGTAVAWYQQKPGQSPKLLIYWASTRHTGVPDRFTGSGSGTD
CDR1          FR2          CDR2    FRR3

FTLTLNNVQSEDLADYFCQQYSTYPTFGSGTKLELKRA
                  CDR3    FR4

Fig. 5

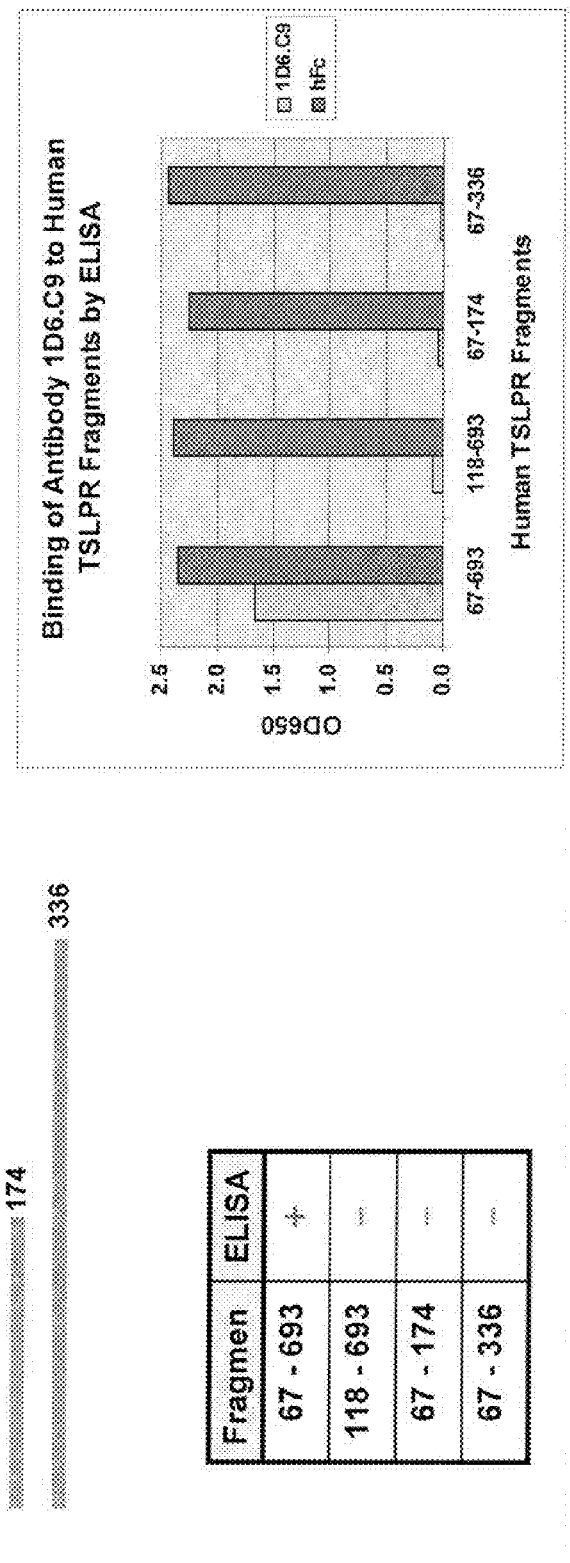
Fig. 8

METHODS AND COMPOSITIONS FOR TREATING ALLERGIC DISEASES

This application is a U.S. National Phase filing of International Application Serial No. PCT/US2007/060379 filed 11 Jan. 2007, and claims priority to U.S. Provisional Application Ser. No. 60/759,625 filed 13 Jan. 2006, the contents of which are incorporated herein by reference in their entirety.

BACKGROUND OF THE INVENTION

Cytokines and immune cells mediate specific physiological mechanisms or pathways, e.g., pathways leading to the various inflammatory disorders. Human thymic stromal lymphopoietin (TSLP) is an IL-7-like cytokine that is produced from human epithelial cells. It promotes B-cell differentiation and also can co-stimulate both thymocytes and mature T-cells. TSLP binds to a specific heterodimeric receptor on human CD11c+ dendritic cells (DC's). The receptor heterodimer consists of a common gamma-like receptor chain (TSLP receptor; TSLPR) and the IL-7R-α chain. See, e.g., Tonozuka et al., Cytogenet. Cell Genet. 93:23-25, 2001; Pandey et al., Nat. Immunol. 1:59-64, 2000; L. S. Park et al., J. Exp. Med. 192:659-670, 2000; and Reche et al., J. Immunol. 167:336-343, 2001. Ligand binding to the receptor induces DC's to secrete $T_H2$-attracting chemokines, TARC (thymus and activation-regulated chemokine) and MDC (macrophage derived chemokine). In addition, TSLP also induces potent DC activation, naïve CD4+ T cell expansion, and subsequent polarization to a $T_H2$ phenotype, producing pro-allergic cytokines interleukin 4 (IL-4), IL-5, IL-13 and tumor necrosis factor-α.

It was also found that TSLP signaling results in activation of the Stat5 transcription factor. Furthermore, both acute and chronic atopic dermatitis patients have been reported to overexpress TSLP in skin lesions, suggesting that TSLP expression is associated with allergic inflammation in vivo. Aside from skin keratinocytes, high level of TSLP expression have also been found in bronchial epithelial cells, smooth muscles and lung fibroblasts, supporting a potential role for TSLP in respiratory allergic indications as well. Moreover, IgE activated mast cells express very high level of TSLP, a mechanism which could participate in the maintenance of the $T_H2$ phenotype.

About 20% of the population in the Western countries suffers from inflammatory disorders, e.g., the allergic diseases, which include asthma, rhinitis, atopic dermatitis, and food allergy. From 50% to 80% of the patients with atopic dermatitis have or develop asthma or allergic rhinitis. To date, there is no cure for allergy induced asthma, atopic dermatitis, and allergic rhinitis. Current treatments, such as beta-2 adrenoceptor antagonists for asthma, Elidel for atopic dermatitis, and H1-antihistamine for allergic rhinitis, are used to target the symptoms. Thus, there is an increased need in the art for better therapies to treat these inflammatory disorders, in particular, allergic inflammation. The present invention addresses this and other problems.

SUMMARY OF THE INVENTION

An embodiment of the invention herein provides an isolated human or humanized antibody or functional fragment thereof with an antigen binding region that is specific for target protein human thymic stromal lymphopoietin receptor (hTSLPR) and the antibody or functional fragment thereof binds to hTSLPR. In a related embodiment, the binding to hTSLPR is determined at least by cell surface hTSLP receptor binding preventing inflammatory mediator release.

In still another embodiment, the invention provides an isolated antigen binding region of an antibody or functional fragment thereof. In certain embodiments, the isolated antigen binding region includes an H-CDR1 region having an amino acid sequence TYGMS (SEQ ID NO: 7), and conservative variants thereof. As described herein, the conservative variants include amino acid residues in any of the amino acid sequences identified. In a related embodiment, the isolated antigen binding region is an H-CDR2 region having an amino acid sequence WINTYSGVPRYADDFKG (SEQ ID NO: 8), and conservative variants thereof. In another related embodiment, the isolated antigen binding region is an H-CDR3 region having an amino acid sequence EGFITTVVGAAGRFVY (SEQ ID NO: 9), and conservative variants thereof.

In another embodiment, the isolated antigen binding region is an L-CDR1 region having an amino acid sequence KASQDVGTAVA (SEQ ID NO: 10), and conservative variants thereof. In still another related embodiment, the isolated antigen binding region is an L-CDR2 region having an amino acid sequence WASTRHT (SEQ ID NO: 11), and conservative variants thereof. In yet another related embodiment, the isolated antigen binding region is an L-CDR3 region having an amino acid sequence QQYSTYPT (SEQ ID NO: 12), and conservative variants thereof.

In another embodiment, the isolated antigen binding region is a heavy chain having the variable region amino acid sequence SEQ ID NO: 5, and a sequence having at least 60, 70, 80, 90 or 95 percent sequence identity in the CDR regions with the CDR region of SEQ ID NO: 5. In a related embodiment, the isolated antigen binding region is a light chain having the variable region amino acid sequence SEQ ID NO: 6, and a sequence having at least 60, 70, 80, 90 or 95 percent sequence identity in the CDR regions with the CDR region of SEQ ID NO: 6.

In another aspect, the present invention provides monoclonal antagonist antibodies against hTSLPR. Some of the anti-TSLPR antibodies of the invention have the same binding specificity as that of a reference antibody that contains a heavy chain variable region sequence of SEQ ID NO: 5 and a light chain variable region sequence of SEQ ID NO: 6. Some of these antibodies are fully human antibodies which exhibit the same binding specificity as that of the reference antibody. Some of the antibodies have a heavy chain complementarity determining region (CDR) sequence of TYGMS (SEQ ID NO: 7), WINTYSGVPRYADDFKG (SEQ ID NO: 8) or EGFITTVVGAAGRFVY (SEQ ID NO: 9); or a light chain CDR sequence of KASQDVGTAVA (SEQ ID NO: 10), WASTRHT (SEQ ID NO: 11), or QQYSTYPT (SEQ ID NO: 12).

Some of the anti-hTSLPR antibodies have heavy chain CDR1, CDR2, and CDR3 sequences, TYGMS (SEQ ID NO: 7), WINTYSGVPRYADDFKG (SEQ ID NO: 8) and EGFITTVVGAAGRFVY (SEQ ID NO: 9), respectively; and light chain CDR1, CDR2, and CDR3 sequences, KASQDVGTAVA (SEQ ID NO: 10), WASTRHT (SEQ ID NO: 11), and QQYSTYPT (SEQ ID NO: 12), respectively. Some other antibodies of the invention contain a heavy chain variable region amino acid sequence that is at least 85% identical to SEQ ID NO: 5 and a light chain variable region amino acid sequence that is at least 85% identical to SEQ ID NO: 6. Some other anti-hTSLPR antibodies of the invention have a heavy chain variable region amino acid sequence that is identical to SEQ ID NO: 5 and a light chain variable region amino acid sequence that is identical to SEQ ID NO: 6.

Some anti-hTSLPR antibodies of the invention are mouse antibodies. Some others are chimeric antibodies. Some of the chimeric antibodies have a human heavy chain constant region and a human light chain constant region. Some other anti-hTSLPR antibodies of the invention are humanized antibodies. Some other anti-hTSLPR antibodies of the invention are fully human antibodies that exhibit the same binding specificity as an antibody that contains a heavy chain variable region sequence of SEQ ID NO: 5 and a light chain variable region sequence of SEQ ID NO: 6. Also provided in the invention are single chain antibodies, e.g., a Fab fragment. Some of the anti-hTSLPR antibodies are of IgG1 isotype. Some other antibodies are of IgG4 isotype.

In another aspect, the invention provides isolated or recombinant polynucleotides (e.g., DNA) that encode a polypeptide containing the heavy chain variable region or the light chain variable region of an anti-hTSLPR antibody of the invention. For example, the polynucleotides can encode an antibody heavy chain that contains heavy chain CDR1, CDR2, and CDR3 sequences, TYGMS (SEQ ID NO: 7), WINTYS-GVPRYADDFKG (SEQ ID NO: 8) and EGFITTV-VGAAGRFVY (SEQ ID NO: 9), respectively. The polynucleotides can also encode an antibody light chain that contains $CDR_{15}$ $CDR_2$, and $CDR_3$ sequences, KASQDVG-TAVA (SEQ ID NO: 10), WASTRHT (SEQ ID NO: 11), and QQYSTYPT (SEQ ID NO: 12), respectively. Some polynucleotides of the invention encode a mature heavy chain variable region sequence that is at least 90% identical to the mature region of SEQ ID NO: 5. Some other polynucleotides encode a mature light chain variable region sequence that is at least 90% identical to the mature region of SEQ ID NO: 6. Some of these polynucleotides encode a mature heavy chain variable region sequence that is identical to the mature region of SEQ ID NO: 5 or a mature light chain variable region sequence that is identical to the mature region of SEQ ID NO: 6.

In another aspect, the invention provides isolated host cells that harbor (1) a recombinant DNA segment encoding a heavy chain of an anti-hTSLPR antibody of the invention, and (2) a second recombinant DNA segment encoding a light chain of the antibody. In some of the host cells, the recombinant DNA segments are respectively operably linked to a first and a second promoter, and are capable of being expressed in the host cells. Some of these host cells express a monoclonal antibody that have heavy chain CDR1, CDR2, and CDR3 sequences, TYGMS (SEQ ID NO: 7), WINTYSGVPRYAD-DFKG (SEQ ID NO: 8) and EGFITTVVGAAGRFVY (SEQ ID NO: 9), respectively; and light chain CDR1, CDR2, and CDR3 sequences, KASQDVGTAVA (SEQ ID NO: 10), WASTRHT (SEQ ID NO: 11), and QQYSTYPT (SEQ ID NO: 12), respectively. Some other host cells express an anti-hTSLPR antibody that contains a mature heavy chain variable region sequence that is at least 90% identical to the mature region of SEQ ID NO: 5; and a mature light chain variable region sequence that is at least 90% identical to the mature region of SEQ ID NO: 6. Some of these host cells express an anti-hTSLPR antibody that contains a mature heavy chain variable region sequence that is identical to the mature region of SEQ ID NO: 5 and a mature light chain variable region sequence that is identical to the mature region of SEQ ID NO: 6. Some of the host cells are non-human mammalian cells.

In another aspect, the invention provides methods of treating an inflammatory disorder in a subject, e.g., a human patient. These methods entail administering to the subject a pharmaceutical composition that contains an effective amount of an anti-hTSLPR antibody. Typically, the anti-hTSLPR antibody has the same binding specificity as that of an anti-hTSLPR antibody that contains a heavy chain variable region sequence of SEQ ID NO: 5 and a light chain variable region sequence of SEQ ID NO: 6. In some of these therapeutic methods, a fully human antibody is employed. In some methods, the anti-TSLPR antibody harbors heavy chain CDR1, CDR2, and CDR3 sequences, TYGMS (SEQ ID NO: 7), WINTYSGVPRYADDFKG (SEQ ID NO: 8) and EGFIT-TVVGAAGRFVY (SEQ ID NO: 9), respectively; and light chain CDR1, CDR2, and CDR3 sequences, KASQDVG-TAVA (SEQ ID NO: 10), WASTRHT (SEQ ID NO: 11), and QQYSTYPT (SEQ ID NO: 12), respectively. In some methods, the employed anti-hTSLPR antibody contains a mature heavy chain variable region sequence that is identical to the mature region of SEQ ID NO: 5, and a mature light chain variable region sequence that is identical to the mature region of SEQ ID NO: 6. Some of the methods are directed to treating subjects that suffer from an allergic inflammatory disease. Examples of allergic inflammatory diseases that are amenable to treatment include atopic dermatitis, asthma, or allergic rhinitis.

In still another embodiment, the invention provides an immunoconjugate made out of a first component which is an antibody or fragment thereof and a second component having a second amino acid sequence. For example, the immunoconjugate is a cytotoxin, or the immunoconjugate is a binding protein or antibody having a binding specificity for a target that is different from hTSLPR.

In another embodiment, the invention provides a kit having an antibody or antibody fragment thereof. In some embodiments, the kit further contains a pharmaceutically acceptable carrier or excipient therefore. In other related embodiments, the antibody in the kit is present in a unit dose. In yet another related embodiment, the kit includes instructions for use in administering to a subject.

A further understanding of the nature and advantages of the present invention may be realized by reference to the remaining portions of the specification and claims.

BRIEF DESCRIPTION OF THE DRAWINGS

FIG. 4 shows nucleotide sequences of the variable regions of the mouse anti-hTSLPR monoclonal antibody 1D6.C9 clone.

FIG. 5 displays the variable region amino acid sequences of the mouse anti-hTSLPR antibody clone 1D6.C9. The complementarity determining regions (CDRs) and the framework regions (FRs) are indicated by underlined residues or italicized residues.

FIG. 8 shows identification of the antibody Binding Domain—the TSLPR antibody binds to a discontinuous epitope

DETAILED DESCRIPTION OF THE INVENTION

Figure 1:
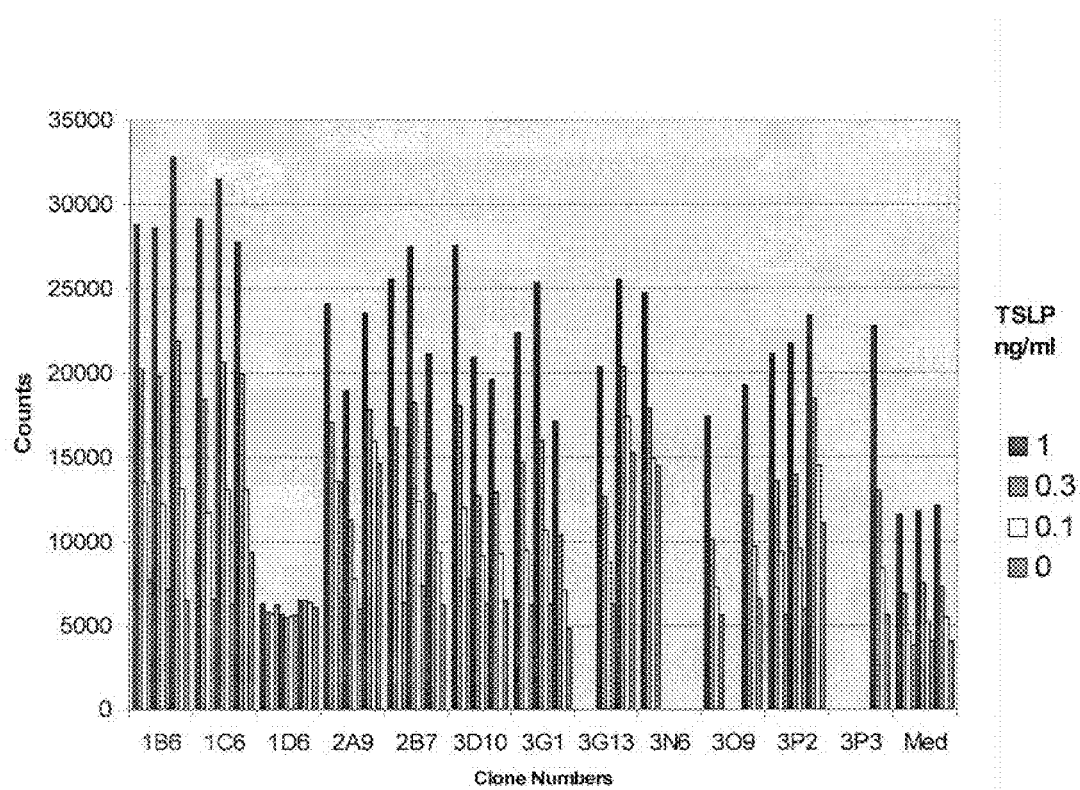
FIG. 1 shows screening for anti-TSLPR antagonist antibodies using an hTSLP-dependent cell proliferation assay in BaF3/hTSLPR/hIL7Rα cells.

The present invention is predicated in part on the development by the present inventors of antagonist antibodies against human TSLPR. The anti-hTSLPR antibodies generated in mouse or chimeric anti-hTSLPR antibodies created in vitro were found to be able to inhibit activities mediated by TSLP signaling, e.g., TSLP-mediated cell proliferation. Thus, these antibodies are useful as therapeutic or prophylactic agents agasint a number of diseases or disorders mediated by or associated with TSLP signaling activities, e.g., allergic inflammatory diseases such as atopic dermatitis and asthma. The following sections provide guidance for making and using the compositions of the invention, and for carrying out the methods of the invention.

I. DEFINITIONS

Unless defined otherwise, all technical and scientific terms used herein have the same meaning as commonly understood by those of ordinary skill in the art to which this invention pertains. The following references provide one of skill with a general definition of many of the terms used in this invention: Oxford Dictionary of Biochemistry and Molecular Biology, Smith et al. (eds.). Oxford University Press (revised ed., 2000); Dictionary of Microbiology and Molecular Biology, Singleton et al. (Eds.), John Wiley & Sons (3PrdP ed., 2002); and A Dictionary of Biology (Oxford Paperback Reference), Martin and Hine (Eds.), Oxford University Press (4PthP ed., 2000). In addition, the following definitions are provided to assist the reader in the practice of the invention.

In order that the present invention may be more readily understood, certain terms are first defined. Additional definitions are set forth throughout the detailed description.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell.

The term "antibody" as referred to herein includes whole antibodies and any antigen binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antigen portion"), as used herein, refers to full length or one or more fragments of an antibody that retain the ability to specifically bind to an antigen (e.g., TSLPR). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g., an isolated antibody that specifically binds TSLPR is substantially free of antibodies that specifically bind antigens other than TSLPR). An isolated antibody that specifically binds TSLPR may, however, have cross-reactivity to other antigens, such as TSLPR molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, as shown in the Examples below, a mouse anti-hTSLPR antibody can be modified by replacing its constant region with the constant region from a human immunoglobulin. Due to the replacement with a human constant region, the chimric antibody can retain its specificity in recognizing human TSLPR while having reduced antigenicity in human as compared to the original mouse antibody.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., *Proc. Natl. Acad. Sci. USA,* 81:6851-6855, 1984; Morrison and Oi, *Adv. Immunol.,* 44:65-92, 1988; Verhoeyen et al., *Science,* 239:1534-1536, 1988; Padlan, *Molec. Immun.,* 28:489-498, 1991; and Padlan, *Molec. Immun.,* 31:169-217, 1994. Other examples of human engineering technology include, but is not limited to Xoma technology disclosed in U.S. Pat. No. 5,766,886.

The term "Humaneering" as used herein refers to a method for converting non-human antibodies into engineered human antibodies (See e.g., KaloBios' Humaneering™ technology).

As used herein, "isotype" refers to the antibody class (e.g., IgM, IgE, IgG such as IgG1 or IgG4) that is provided by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human TSLPR" refers to an antibody that binds to human TSLPR with a $K_D$ of $200 \times 10^{-12}$ M or less, $150 \times 10^{-12}$ M or less, or $100 \times 10^{-12}$ M or less.

The term "binding specificity" as used herein refers to the ability of an individual antibody combining site to react with only one antigenic determinant. The combining site of the antibody is located in the Fab portion of the molecule and is constructed from the hypervariable regions of the heavy and light chains. Binding affinity of an antibody is the strength of the reaction between a single antigenic determinant and a single combining site on the antibody. It is the sum of the attractive and repulsive forces operating between the antigenic determinant and the combining site of the antibody. Affinity is the equilibrium constant that describes the antigen-antibody reaction.

Specific binding between two entities means a binding with an equilibrium constant ($K_A$) of at least $1 \times 10^7$ M$^{-1}$, $10^8$ M$^{-1}$, $10^9$ M$^{-1}$, or $10^{10}$ M$^{-1}$. The phrase "specifically (or selectively) binds" to an antibody (e.g., an anti-hTSLPR antibody) refers to a binding reaction that is determinative of the presence of a cognate antigen (e.g., a human TSLPR polypeptide) in a heterogeneous population of proteins and other biologics. In addition to the equilibrium constant ($K_A$) noted above, an anti-hTSLPR antibody of the invention typically also has a dissociation constant ($K_d$) of about $1 \times 10^{-2}$ s$^{-1}$, $1 \times 10^{-3}$ s$^{-1}$, $1 \times 10^{-4}$ s$^{-1}$ or lower, and binds to human TSLPR with an affinity that is at least two-fold greater than its affinity for binding to a non-specific antigen (e.g., BSA). The phrases "an antibody recognizing an antigen" and "an antibody specific for an antigen" are used interchangeably herein with the term "an antibody which binds specifically to an antigen".

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TOG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch, *J. Mol. Biol.* 48:443, 1970, by the search for similarity method of Pearson and Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., *Current Protocols in Molecular Biology*, John Wiley & Sons, Inc. (ringbou ed., 2003)).

Two examples of algorithms that are suitable for determining percent sequence identity and sequence similarity are the BLAST and BLAST 2.0 algorithms, which are described in Altschul et al., *Nuc. Acids Res.* 25:3389-3402, 1977; and Altschul et al., *J. Mol. Biol.* 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 1, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "inflammatory disease or condition" refers to any condition characterized by local inflammation at a site of injury or infection and includes autoimmune diseases, certain forms of infectious inflammatory states, undesirable neutrophil activity characteristic of organ transplants or other implants and virtually any other condition characterized by unwanted neutrophil accumulation at a local tissue site. These conditions include but are not limited to meningitis, cerebral edema, arthritis, nephritis, adult respiratory distress syndrome, pancreatitis, myositis, neuritis, connective tissue diseases, phlebitis, arteritis, vasculitis, allergy, anaphylaxis, ehrlichiosis, gout, organ transplants and/or ulcerative colitis.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "treating" includes the administration of compounds or agents to prevent or delay the onset of the symptoms, complications, or biochemical indicia of a disease (e.g., an allegic inflammatory disease), alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

The phrase "signal transduction pathway" or "signaling pathway" (e.g., the TSLP signaling pathway) refers to at least one biochemical reaction, but more commonly a series of biochemical reactions, which result from interaction of a cell with a stimulatory compound or agent. Thus, the interaction of a stimulatory compound (e.g., TSLP) with a cell generates a "signal" that is transmitted through the signal transduction pathway, ultimately resulting in a cellular response, e.g., an immune response.

II. ANTAGONIST ANTIBODIES AGAINST HUMAN TSLPR

1. Overview

The invention provides antibodies that specifically bind to human TSLPR. These anti-hTSLPR antibodies are capable of antagonizing TSLP mediated signaling activities, e.g., TSLP mediated cell proliferation as described in the Examples below. General methods for preparation of monoclonal or polyclonal antibodies are well known in the art. See, e.g., Harlow & Lane, *Using Antibodies, A Laboratory Manual*, Cold Spring Harbor Laboratory Press, Cold Spring Harbor, N.Y., 1998; Kohler & Milstein, *Nature* 256:495-497, 1975; Kozbor et al., *Immunology Today* 4:72, 1983; and Cole et al., pp. 77-96 in *Monoclonal Antibodies and Cancer Therapy*, 1985.

Preferably, the anti-hTSLPR antibodies of the invention are monoclonal like the mouse monoclonal antibody raised against human TSLPR (clone 1D6.C9) as described in the Examples below. Monoclonal antibodies refer to antibodies derived from a single clone. Any technique for producing monoclonal antibody can be employed to produce anti-hTSLPR antibodies of the invention, e.g., viral or oncogenic transformation of B lymphocytes. One animal system for preparing hybridomas is the murine system. Hybridoma production in the mouse is a very well-established procedure. As illustrated in the Examples below, monoclonal anti-hTSLPR antibodies can be generated by immunizing a non-human animal (e.g., mouse) with an hTSLPR polypeptide, or a fragment, fusion protein, or varant thereof. B cells isolated from the animal are then fused to myeloma cells to generate antibody-producing hybridomas. Monoclonal mouse anti-hTSLPR antibodies can be obtained by screening the hybridomas in an ELISA assay using an hTSLPR polypeptide or fusion protein. Immunization protocols and techniques for isolation of immunized splenocytes for fusion are known in the art. Fusion partners (e.g., murine myeloma cells) and fusion procedures are also well known in the art, e.g., Harlow & Lane, supra.

The amino acid sequences of the heavy chain (SEQ ID NO: 5) and light chain variable regions (SEQ ID NO: 6) of the exemplary mouse anti-TSLPR antibody described in the Examples below are shown in FIG. 5. Also as indicated in the figure, the CDR sequences of the heavy chain variable region of this antibody are TYGMS (CDR1; SEQ ID NO: 7), WIN-TYSGVPRYADDFKG (CDR2; SEQ ID NO: 8), and EGFIT-TVVGAAGRFVY (CDR3; SEQ ID NO: 9). The CDR sequences of the light chain variable region are KASQDVG-TAVA (CDR1; SEQ ID NO: 10), WASTRHT (CDR2; SEQ ID NO: 11), and QQYSTYPT (CDR3; SEQ ID NO: 12).

Antibodies interact with target antigens predominantly through amino acid residues that are located in the six heavy and light chain complementarity determining regions (CDR's). Typically, the anti-hTSLPR antibodies of the invention have at least one of their heavy chain CDR sequences or light chain CDR sequences identical to the corresponding CDR sequences shown in FIG. 5. Some of these anti-hTSLPR antibodies of the invention have the same binding specificity as that of the exemplified mouse anti-TSLPR antibody (clone 1D6.C9) disclosed in the Examples below. These antibodies can compete with the mouse anti-hTSLPR antibody (clone 1D6.C9) for binding to hTSLPR. Some anti-hTSLPR antibodies of the invention have all CDR sequences in their variable regions of the heavy chain and light chain respectively identical to the corresponding CDR sequences shown in FIG. 5. Thus, these anti-hTSLPR antibodies have the three heavy chain CDR sequences respectively identical to SEQ ID NO: 7, SEQ ID NO:8, and SEQ ID NO: 9, and the three light chain CDR sequences respectively identical to SEQ ID NO: 10, SEQ ID NO: 11, and SEQ ID NO: 12.

In addition to having CDR sequences respectively identical to the corresponding CDR sequences of the mouse anti-hTSLPR antibody (clone 1D6.C9), some of the anti-hTSLPR antibodies of the invention have their entire heavy chain and light chain variable region sequences respectively identical to the corresponding variable region sequences of the mouse antibody as shown in FIG. 5 (i.e., SEQ ID NO: 5 and SEQ ID NO: 6). In some other embodiments, other than the identical CDR sequences, the antibodies contain amino acid residues in the framework portions of the variable regions that are different from the corresponding amino acid residues shown in FIG. 5 (e.g., some of the humanized anti-hTSLPR antibodies described below). Nevertheless, these antibodies typically have their entire variable region sequences that are substantial identical (e.g., 75%, 85%, 90%, 95%, or 99%) to the corresponding variable region sequences shown in FIG. 5.

The anti-hTSLPR antibodies of the invention can be an intact antibody which contains two heavy chains and two light chains. They can also be antigen-binding fragments of an intact antibody or single chain antibodies. The anti-hTSLPR antibodies of the invention include antibodies produced in a non-human animal (e.g., the mouse anti-hTSLPR antibody shown in FIG. 5). They also include modified antibodies which are modified forms of the mouse anti-hTSLPR antibody shown in FIG. 5. Often, the modified antibodies are recombinant antibodies which have similar or improved properties relative to that of the exemplified mouse antibody. For example, the mouse anti-hTSLPR antibody exemplified in the Examples below can be modified by deleting the constant region and replacing it with a different constant region that can lead to increased half-life, e.g., serum half-life, stability or affinity of the antibody. The modified antibodies can be created, e.g., by constructing expression vectors that include the CDR sequences from the mouse antibody grafted onto framework sequences from a different antibody with different properties (Jones et al. 1986, *Nature* 321, 522-525). Such framework sequences can be obtained from public DNA databases.

Some of the modified antibodies are chimeric antibodies which contain partial human immunoglobulin sequences (e.g., constant regions) and partial non-human immunoglobulin sequences (e.g., the mouse anti-hTSLPR antibody variable region sequences shown in FIG. 5). Some other modified antibodies are humanized antibodies. Generally, a humanized antibody has one or more amino acid residues introduced into it from a source that is non-human. Methods for humanizing non-human antibodies are well known in the art, e.g., U.S. Pat. Nos. 5,585,089 and 5,693,762; Jones et al., Nature 321: 522-25, 1986; Riechmann et al., Nature 332: 323-27, 1988; and Verhoeyen et al., Science 239: 1534-36, 1988. These methods can be readily employed to generate humanized anti-hTSLPR antibodies of the invention by substituting at least a portion of a CDR from a non-human anti-hTSLPR antibody for the corresponding regions of a human antibody. In some embodiments, the humanized anti-hTSLPR antibodies of the invention have all three CDRs in each immunoglobulin chain from the mouse anti-hTSLPR antibody shown in FIG. 5 grafted into corresponding human framework regions.

The anti-hTSLPR antibodies described above can undergo non-critical amino-acid substitutions, additions or deletions in both the variable and constant regions without loss of binding specificity or effector functions, or intolerable reduction of binding affinity. Usually, antibodies incorporating such alterations exhibit substantial sequence identity to a reference antibody (e.g., the mouse anti-hTSLPR antibody shown in FIG. 5) from which they were derived. For example, the mature light chain variable regions of some of the anti-hTSLPR antibodies of the invention have at least 75% or at least 85% sequence identity to the sequence of the mature light chain variable region of the anti-hTSLPR antibody shown in FIG. 5. Similarly, the mature heavy chain variable regions of the antibodies typically show at least 75% or at least 85% sequence identity to the sequence of the mature heavy chain variable region of the anti-hTSLPR antibody shown in FIG. 5. Some of the modified anti-hTSLPR antibodies have the same specificity and increased affinity compared with the mouse anti-hTSLPR antibody (clone 1D6.C9) shown in FIG. 5. Usually, the affinity of the modified anti-hTSLPR antibodies (e.g. humanized antibodies) have a binding affinity that is the same or better than the original mouse antibody. The binding affinity of the modified antibodies is at least 70%, 75%, 80%, 85%, 90%, 95% or 100% of the original mouse antibody.

2. Chimeric and Humanized Anti-hTSLPR Antibodies

Some of the anti-hTSLPR antibodies of the invention are chimeric (e.g., mouse/human) antibodies which are made up of regions from a non-human anti-hTSLPR antibody antagonist together with regions of human antibodies. For example, a chimeric H chain can comprise the antigen binding region of the heavy chain variable region of the mouse anti-TSLPR antibody (e.g., the sequence shown in SEQ ID NO: 5) linked to at least a portion of a human heavy chain constant region. This chimeric heavy chain may be combined with a chimeric L chain that comprises the antigen binding region of the light chain variable region of the mouse anti-hTSLPR antibody (e.g., the sequence shown in SEQ ID NO: 6) linked to at least a portion of the human light chain constant region.

Chimeric anti-hTSLPR antibodies of the invention can be produced in accordance with the disclosure in the Examples below as well as methods known in the art. For example, a gene encoding the heavy chain or light chain of a murine anti-hTSLPR monoclonal antibody molecule can be digested with restriction enzymes to remove the murine Fc region, and substituted with the equivalent portion of a gene encoding a human Fc constant region. Expression vectors and host cells suitable for expression of recombinant antibodies and humanized antibodies in particular, are well known in the art. Vectors expressing chimeric genes encoding anti-hTSLPR immunoglobulin chains can be constructed using standard recombinant techniques, e.g., Sambrook et al., *Molecular Cloning: A Laboratory Manual*, Cold Spring Harbor Press (3rd ed., 2001); and Brent et al., *Current Protocols in Molecular Biology*, John Wiley & Sons, Inc. (ringbou ed., 2003). Human constant region sequences can be selected from various reference sources, including but not limited to those listed in Kabat et al., Sequences of Proteins of Immunological Interest, Fifth Edition, U.S. Department of Health and Human Services, U.S. Government Printing Office, 1991. More specific teachings of producing chimeric antibodies by DNA recombination have also been taught in the art, e.g., Robinson et al., International Patent Publication PCT/US86/02269; Akira, et al. European Patent Application 184,187; Taniguchi, M., European Patent Application 171,496; Morrison et alt., European Patent Application 173,494; Neuberger et al., International Application WO 86/01533; Cabilly et al. U.S. Pat. No. 4,816,567; Cabilly et al., European Patent Application 125,023; Better (1988) Science 240:1041-1043; Liu (1987) PNAS 84:3439-3443; Liu (1987) J. Immunol. 139:3521-3526; Sun (1987) PNAS 84:214-218; Nishimura (1987) Canc. Res. 47:999-1005; Wood (1985) Nature 314:446-449; Shaw (1988) J. Natl. Cancer Inst. 80:1553-1559).

Chimeric antibodies which have the entire variable regions from a non-human antibody can be further humanized to reduce antigenicity of the antibody in human. This is typically accompanished by replacing certain sequences or amino acid residues in the Fv variable regions (framework regions or non-CDR regions) with equivalent sequences or amino acid residues from human Fv variable regions. These additionally substituted sequences or amino acid residues are usually not directly involved in antigen binding. More often, humanization of a non-human antibody proceeds by substituting only the CDRs of a non-human antibody (e.g., the mouse antibody shown in FIG. 5) for the CDRs in a human antibody. In some cases, this is followed by replacing some additional residues in the human framework regions with the corresponding residues from the non-human donor antibody. Such additional grafting is often needed to improve binding to the antigen. This is because humanized antibodies which only have CDRs grafted from a non-human antibody can have less than perfect binding activities as compared to that of the non-human donor antibody. Thus, in addition to the CDRs, humanized anti-hTSLPR antibodies of the invention can often have some amino acids residues in the human framework region replaced with corresponding residues from the non-human donor antibody (e.g., the mouse antibody shown in FIG. 5). Methods for generating humanized antibodies by CDR substitution, including criteria for selecting framework residues for replacement, are well known in the art. For example, in addition to the above noted art relating to producing chimeric antibodies, additional teachings on making humanized antibodies are provided in, e.g., Winter et al., UK Patent Application GB 2188638A (1987), U.S. Pat. No. 5,225,539; Jones (1986) Nature 321:552-525; Verhoeyan et al. 1988 Science 239:1534; and Beidler (1988) J. Immunol. 141:4053-4060. CDR substitution can also be carried out using oligonucleotide site-directed mutagenesis as described in, e.g., WO 94/10332 entitled, Humanized Antibodies to Fc Receptors for Immunoglobulin G on Human Mononuclear Phagocytes.

The chimeric or humanized anti-hTSLPR antibodies of the invention may be monovalent, divalent, or polyvalent immunoglobulins. For example, a monovalent chimeric antibody is a dimer (HL) formed by a chimeric H chain associated through disulfide bridges with a chimeric L chain, as noted above. A divalent chimeric antibody is a tetramer ($H_2 L_2$) formed by two HL dimers associated through at least one disulfide bridge. A polyvalent chimeric antibody is based on an aggregation of chains.

3. Human Anti-hTSLPR Antibodies

In addition to chimeric or humanized anti-hTSLPR antibodies, also included in the invention are fully human antibodies that exhibit the same binding specificity and comparable or better binding affinity. For example, the human antibodies can have the same or better binding characteristics relative to that of a reference nonhuman antibody which contains a heavy chain variable region sequence of SEQ ID NO:

5 and a light chain variable region sequence of SEQ ID NO: 6. Compared to the chimeric or humanized antibodies, the human anti-hTSLPR antibodies of the invention have further reduced antigenicity when administered to human subjects.

The human anti-hTSLPR antibodies can be generated using methods that are known in the art. For example, an in vivo method for replacing a nonhuman antibody variable region with a human variable region in an antibody while maintaining the same or providing better binding characteristics relative to that of the nonhuman antibody has been disclosed in U.S. patent application Ser. No. 10/778,726 (Publication No. 20050008625). The method relies on epitope guided replacement of variable regions of a non-human reference antibody with a fully human antibody. The resulting human antibody is generally unrelated structurally to the reference nonhuman antibody, but binds to the same epitope on the same antigen as the reference antibody. Briefly, the serial epitope-guided complementarity replacement approach is enabled by setting up a competition in cells between a "competitor" and a library of diverse hybrids of the reference antibody ("test antibodies") for binding to limiting amounts of antigen in the presence of a reporter system which responds to the binding of test antibody to antigen. The competitor can be the reference antibody or derivative thereof such as a single-chain Fv fragment. The competitor can also be a natural or artificial ligand of the antigen which binds to the same epitope as the reference antibody. The only requirements of the competitor are that it binds to the same epitope as the reference antibody, and that it competes with the reference antibody for antigen binding. The test antibodies have one antigen-binding V-region in common from the nonhuman reference antibody, and the other V-region selected at random from a diverse source such as a repertoire library of human antibodies. The common V-region from the reference antibody serves as a guide, positioning the test antibodies on the same epitope on the antigen, and in the same orientation, so that selection is biased toward the highest antigen-binding fidelity to the reference antibody. Identification of the TSLPR binding domain was identified by epitope mapping and is shown in FIG. 8. The TSLPR antibody binds to a discontinous epitope.

Many types of reporter system can be used to detect desired interactions between test antibodies and antigen. For example, complementing reporter fragments may be linked to antigen and test antibody, respectively, so that reporter activation by fragment complementation only occurs when the test antibody binds to the antigen. When the test antibody- and antigen-reporter fragment fusions are co-expressed with a competitor, reporter activation becomes dependent on the ability of the test antibody to compete with the competitor, which is proportional to the affinity of the test antibody for the antigen. Other reporter systems that can be used include the reactivator of an auto-inhibited reporter reactivation system (RAIR) as disclosed in U.S. patent application Ser. No. 10/208,730 (Publication No. 20030198971), or competitive activation system disclosed in U.S. patent application Ser. No. 10/076,845 (Publication No. 20030157579).

With the serial epitope-guided complementarity replacement system, selection is made to identify cells expresses a single test antibody along with the competitor, antigen, and reporter components. In these cells, each test antibody competes one-on-one with the competitor for binding to a limiting amount of antigen. Activity of the reporter is proportional to the amount of antigen bound to the test antibody, which in turn is proportional to the affinity of the test antibody for the antigen and the stability of the test antibody. Test antibodies are initially selected on the basis of their activity relative to that of the reference antibody when expressed as the test antibody. The result of the first round of selection is a set of "hybrid" antibodies, each of which is comprised of the same non-human V-region from the reference antibody and a human V-region from the library, and each of which binds to the same epitope on the antigen as the reference antibody. One of more of the hybrid antibodies selected in the first round will have an affinity for the antigen comparable to or higher than that of the reference antibody.

In the second V-region replacement step, the human V-regions selected in the first step are used as guide for the selection of human replacements for the remaining non-human reference antibody V-region with a diverse library of cognate human V-regions. The hybrid antibodies selected in the first round may also be used as competitors for the second round of selection. The result of the second round of selection is a set of fully human antibodies which differ structurally from the reference antibody, but which compete with the reference antibody for binding to the same antigen. Some of the selected human antibodies bind to the same epitope on the same antigen as the reference antibody. Among these selected human antibodies, one or more binds to the same epitope with an affinity which is comparable to or higher than that of the reference antibody.

Using one of the mouse or chimeric anti-hTSLPR antibodies described above as the reference antibody, this method can be readily employed to generate human antibodies that bind to human TSLPR with the same binding specificity and the same or better binding affinity. In addition, such human anti-hTSLPR antibodies can also be commercially obtained from companies which customarily produce human antibodies, e.g., KaloBios, Inc. (Mountain View, Calif.).

4. Other Types of Anti-hTSLPR Antibodies

The anti-hTSLPR antibodies of the invention also include single chain antibodies, bispecific antibodies and multi-specific antibodies. In some embodiments, the antibodies of the invention are single chain antibodies. Single chain antibodies contain in a single stably-folded polypeptide chain the antigen-binding regions from both the heavy chain and the light chain. As such, single chain antibodies typically retain the binding specificity and affinity of monoclonal antibodies but are of considerably small size than classical immunoglobulins. For certain applications, the anti-hTSLPR single chain antibodies of the invention may provide many advantageous properties as compared to an intact anti-hTSLPR antibody. These include, e.g., faster clearance from the body, greater tissue penetration for both diagnostic imaging and therapy, and a significant decrease in immunogenicity when compared with mouse-based antibodies. Other potential benefits of using single chain antibodies include enhanced screening capabilities in high throughput screening methods and the potential for non-parenteral application.

Single chain anti-hTSLPR antibodies of the invention can be prepared using methods that have been described in the art. Examples of such techniques include those described in U.S. Pat. Nos. 4,946,778 and 5,258,498; Huston et al., *Methods in Enzymology* 203:46-88, 1991; Shu et al., *Proc. Natl. Acad. Sci. USA* 90:7995-7999, 1993; and Skerra et al, *Science* 240: 1038-1040, 1988.

In some embodiments, the invention provides anti-hTSLPR antibodies derivatized or linked to another functional molecule to generate a bispecific or multispecific molecule which binds to multiple binding sites or target epitopes. The functional molecule includes another peptide or protein (e.g., a cytokine, a cytotoxic agent, an immune stimulatory or inhibitory agent, a Fab' fragment or other antibody binding fragment as discussed above). For example, an anti-hTSLPR antibody or antigen-binding portion thereof can be functionally linked (e.g., by chemical coupling, genetic fusion, non-covalent association or otherwise) to one or more other binding molecules, such as another antibody, antibody fragment, peptide or binding mimetic. Thus, the bispecific and multispecific anii-hTSLPR antibodies of the invention comprises at least one monoclonal anti-hTSLPR antibody or antigen binding fragment thereof with a first binding specificity for human TSLPR and a second binding specificity for a second target epitope. The second target epitope can be an Fc receptor, e.g., human FcγRI or a human Fcγ receptor. Therefore, the invention includes bispecific and multispecific molecules capable of binding both to FcγRI, FcγR or FcεR expressing effector cells (e.g., monocytes, macrophages or polymorphonuclear cells (PMNs)), and to target cells expressing human TSLPR (e.g., human CD11c+ dendritic cells). These multispecific (e.g., bispecific or multispecific) molecules target human TSLPR expressing cells to effector cells, and trigger Fc receptor-mediated effector cell activities, such as phagocytosis of a human TSLPR-expressing cells, antibody dependent cell-mediated cytotoxicity (ADCC), cytokine release, or generation of superoxide anion.

Bispecific and multispecific anti-hTSLPR molecules of the present invention can be made by methods that have been described in the art. These include chemical techniques (see, e.g., Kranz, Proc. Natl. Acad. Sci. USA 78:5807, 1981), polydoma techniques (see, e.g., U.S. Pat. No. 4,474,893), or recombinant DNA techniques. Bispecific and multispecific molecules of the present invention can also be prepared by conjugating the constituent binding specificities, e.g., the anti-FcR and anti-human TSLPR binding specificities, using methods known in the art and as described herein. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), N-succinimidyl-3-(2-pyridyldithio)propionate (SPDP), and sulfosuccinimidyl 4-(N-maleimidomethyl)cyclohaxane-1-carboxylate (sulfo-SMCC). When the binding specificities are antibodies (e.g., two humanized antibodies), they can be conjugated via sulfhydryl bonding of the C-terminus hinge regions of the two heavy chains. The hinge region can be modified to contain an odd number of sulfhydryl residues, e.g., one, prior to conjugation.

Binding of the bispecific and multispecific molecules to their specific targets can be confirmed by enzyme-linked immunosorbent assay (ELISA), a radioimmunoassay (RIA), or a Western Blot Assay. Each of these assays generally detects the presence of protein-antibody complexes of particular interest by employing a labeled reagent (e.g, an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, e.g., Weintraub, B., *Principles of Radioimmunoassays*, Seventh Training Course on Radioligand-Assay Techniques, The Endocrine Society, March, 1986). The radioactive isotope can be detected by such means as the use of a y counter or a scintillation counter or by autoradiography.

III. POLYNUCLEOTIDES, VECTORS AND HOST CELLS FOR PRODUCING ANTI-HTSLPR ANTIBODIES

The invention provides substantially purified polynucleotides (DNA or RNA) which encode polypeptides comprising segments or domains of the anti-hTSLPR antibody chains described above. Some of the polynucleotides of the invention comprise the nucleotide sequence of the heavy chain variable region shown in SEQ ID NO: 13 and/or the nucleotide sequence of the light chain variable region shown in SEQ ID NO: 14. Some other polynucleotides of the invention comprise nucleotide sequences that are substantially identical (e.g., at least 65, 80%, 95%, or 99%) to the nucleotide sequences of SEQ ID NO: 13 or SEQ ID NO: 14. When expressed from appropriate expression vectors, polypeptides encoded by these polynucleotides are capable of exhibiting antigen binding capacity.

Also provided in the invention are polynucleotides which encode at least one CDR region and usually all three CDR regions from the heavy or light chain of the anti-hTSLPR antibody shown in FIG. 5. Some other polynucleotides encode all or substantially all of the variable region sequence of the heavy chain and/or the light chain of the anti-hTSLPR antibody shown in FIG. 5. For example, some of these polynucleotides encode the amino acid sequence of the heavy chain variable region shown in SEQ ID NO: 5 and/or the amino acid sequence of the light chain variable region shown in SEQ ID NO: 6. Because of the degeneracy of the code, a variety of nucleic acid sequences will encode each of the immunoglobulin amino acid sequences.

The polynucleotides of the invention can encode only the variable region sequence of an anti-hTSLPR antibody. They can also encode both a variable region and a constant region of the antibody. Some of polynucleotide sequences of the invention nucleic acids encode a mature heavy chain variable region sequence that is substantially identical (e.g., at least 80%, 90%, or 99%) to the mature heavy chain variable region sequence of the 1D6.C9 mouse anti-hTSLPR antibody shown in SEQ ID NO: 5. Some other polynucleotide sequences encode a mature light chain variable region sequence that is substantially identical to the mature light chain variable region sequence of the 1D6.C9 mouse antibody shown in SEQ ID NO: 6. Some of the polynucleotide sequences encode a polypeptide that comprises variable regions of both the heavy chain and the light chain of the mouse antibody. Some other polynucleotides encode two polypeptide segments that respectively are substantially identical to the variable regions of the heavy chain and the light chain of the mouse antibody.

The polynucleotide sequences can be produced by de novo solid-phase DNA synthesis or by PCR mutagenesis of an existing sequence (e.g., sequences as described in the Examples below) encoding an anti-hTSLPR antibody or its binding fragment. Direct chemical synthesis of nucleic acids can be accomplished by methods known in the art, such as the phosphotriester method of Narang et al., 1979, *Meth. Enzymol.* 68:90; the phosphodiester method of Brown et al., *Meth. Enzymol.* 68:109, 1979; the diethylphosphoramidite method of Beaucage et al., *Tetra. Lett.,* 22:1859, 1981; and the solid support method of U.S. Pat. No. 4,458,066. Introducing mutations to a polynucleotide sequence by PCR can be performed as described in, e.g., *PCR Technology: Principles and Applications for DNA Amplification*, H. A. Erlich (Ed.), Freeman Press, NY, N.Y., 1992; *PCR Protocols: A Guide to Methods and Applications*, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the anti-hTSLPR antibodies described above. Various expression vectors can be employed to express the polynucleotides encoding the anti-TSLPR antibody chains or bidning fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., *Nat Genet* 15:345, 1997). For example, nonviral vectors useful for expression of the anti-hTSLPR polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, *Annu. Rev. Microbiol.* 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-hTSLPR antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an anti-hTSLPR antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., *Results Probl. Cell Differ.* 20:125, 1994; and Bittner et al., *Meth. Enzymol.*, 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-hTSLPR antibody sequences. More often, the inserted anti-hTSLPR antibody sequences are linked to a signal sequences before inclusion in the vector. Vectors to be used to receive sequences encoding anti-hTSLPR antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-hTSLPR antibody chains can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella*, *Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-hTSLPR polypeptides of the invention. Insect cells in combination with baculovirus vectors can also be used.

In some preferred embodiments, mammalian host cells are used to express and produce the anti-hTSLPR polypeptides of the present invention. For example, they can be either a hybridoma cell line expressing endogenous immunoglobulin genes (e.g., the 1D6.C9 myeloma hybridoma clone as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, New York, N.Y., 1987. Expression vectors for mammalian host cells can include expression control sequences, such as an origin of replication, a promoter, and an enhancer (see, e.g., Queen, et al., *Immunol. Rev.* 89:49-68, 1986); and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, *Cell* 88:223, 1997), agent-enhanced uptake of DNA, and ex vivo transduction. For long-term, high-yield production of recombinant proteins, stable expression will often be desired. For example, cell lines which stably express anti-hTSLPR antibody chains or binding fragments can be prepared using expression vectors of the invention which contain viral origins of replication or endogenous expression elements and a selectable marker gene.

Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

IV. PROPERTIES OF THE ANTI-HTSLPR ANTIBODIES

Once an anti-hTSLPR antibody described above is expressed from an expression vector in a host cell or endogenously in a hybridoma, they can be readily purified from culture media and host cells. Usually, antibody chains are expressed with signal sequences and are thus released to the culture media. However, if antibody chains are not naturally secreted by host cells, the antibody chains can be released by treatment with mild detergent. Antibody chains can then be purified by conventional methods including ammonium sulfate precipitation, affinity chromatography to immobilized target, column chromatography, gel electrophoresis and the like. These methods are all well known and routinely practiced in the art, e.g., Scopes, *Protein Purification*, Springer-Verlag, NY, 1982; and Harlow & Lane, supra.

By way of example, selected hybridomas expressing anti-hTSLPR antibodies of the invention can be grown in two-liter spinner-flasks for monoclonal antibody purification. Supernatants can be filtered and concentrated before affinity chromatography with protein A-sepharose or protein G-sepharose (Pharmacia; Piscataway, N.J.). Fluted IgG can be checked by gel electrophoresis and high performance liquid chromatography to ensure purity. The buffer solution can be exchanged into PBS, and the concentration can be determined by OD280 reading. The monoclonal antibodies can be aliquoted and stored at −80° C.

Irrespective of their method of preparation, the anti-hTSLPR monoclonal antibodies of the present invention bind specifically to hTSLPR or an antigenic fragment thereof. Specific binding exists when the dissociation constant for antibody binding to hTSLPR or an antigenic fragment thereof is $\leq 1$ µM, preferably $\leq 100$ nM, and most preferably $\leq 1$ nM. The ability of an antibody to bind to hTSLPR can be detected by labelling the antibody of interest directly, or the antibody may be unlabelled and binding detected indirectly using various sandwich assay formats. See, e.g., Harlow & Lane, supra. Antibodies having such binding specificity are more likely to share the advantageous properties exhibited by the 11D6.C9 mouse anti-hTSLPR antibody discussed in the Examples below.

The anti-TSLPR monoclonal antibodies of the invention are capable of antagonizing the signaling activities mediated by TSLP. These activities include, e.g., secretion of $T_H2$-attracting chemokines by dendritic cells such as TARC and MDC; activation of dendritic cells, naïve CD4+ T cell expansion and polarization to a $T_H2$ phenotype, production of pro-allergic cytokines such as IL-4, IL-5, IL-13 TNFα. A number of assays can be employed to determine whether an anti-hTSLPR antibody can inhibit TSLP mediated cellular activities. These include, e.g., any of the assays described in the Examples such as the cell proliferation assay using Ba/F3/hTSLPR/hIL7Rα cells, the luciferase reporter assay using Ba/F3/hTSLPR/IL7Rα/Stat5-Luc cells, and the TARC secretion assay. Additional assays for measuring TSLP signaling activities have also been described in the art. See, e.g., Reche et al., J. Immunol., 167:336-43, 2001; and Isaksen et al., J Immunol. 168:3288-94, 2002.

In some embodiments, the anti-hTSLPR antibodies of the invention block or compete with binding of a reference anti-hTSLPR antibody having variable region sequences shown in FIG. 5 (e.g., the mouse 1D6.C9 antibody or a chimeric antibody thereof described in the Examples below) to an hTSLPR polypeptide. These can be fully human anti-hTSLPR antibodies described above. They can also be other mouse, chimeric or humanized anti-hTSLPR antibodies which bind to the same epitope as the reference antibody. The capacity to block or compete with the reference antibody binding indicates that an anti-hTSLPR antibody under test binds to the same or similar epitope as that defined by the reference antibody, or to an epitope which is sufficiently proximal to the epitope bound by the reference anti-hTSLPR antibody. Such antibodies are especially likely to share the advantageous properties identified for the reference antibody. The capacity to block or compete with the reference antibody may be determined by, e.g., a competition binding assay. With a competition binding assay, the antibody under test is examined for ability to inhibit specific binding of the reference antibody to a common antigen, such as a TSLPR polypeptide. A test antibody competes with the reference antibody for specific binding to the antigen if an excess of the test antibody substantially inhibits binding of the reference antibody. Substantial inhibition means that the test antibody reduces specific binding of the reference antibody usually by at least 10%, 25%, 50%, 75%, or 90%.

There are a number of known competition binding assays that can be used to assess competition of an anti-hTSLPR antibody with the reference anti-hTSLPR antibody for binding to human TSLPR. These include, e.g., solid phase direct or indirect radioimmunoassay (RIA), solid phase direct or indirect enzyme immunoassay (EIA), sandwich competition assay (see Stahli et al., Methods in Enzymology 9:242-253, 1983); solid phase direct biotin-avidin EIA (see Kirkland et al., J. Immunol. 137:3614-3619, 1986); solid phase direct labeled assay, solid phase direct labeled sandwich assay (see Harlow & Lane, supra); solid phase direct label RIA using I-125 label (see Morel et al., Molec. Immunol. 25:7-15, 1988); solid phase direct biotin-avidin EIA (Cheung et al., Virology 176:546-552, 1990); and direct labeled RIA (Moldenhauer et al., Scand. J. Immunol.32:77-82, 1990). Typically, such an assay involves the use of purified antigen bound to a solid surface or cells bearing either of these, an unlabelled test anti-hTSLPR antibody and a labelled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

To determine if the selected anti-TSLPR monoclonal antibodies bind to unique epitopes, each antibody can be biotinylated using commercially available reagents (e.g., reagents from Pierce, Rockford, Ill.). Competition studies using unlabeled monoclonal antibodies and biotinylated monoclonal antibodies can be performed using a TSLPR polypeptide coated ELISA plates. Biotinylated MAb binding can be detected with a strep-avidin-alkaline phosphatase probe. To determine the isotype of a purified anti-TSLPR antibody, isotype ELISAs can be performed. For example, wells of microtiter plates can be coated with 1 µg/ml of anti-human IgG overnight at 4° C. After blocking with 1% BSA, the plates are reacted with 1 µg/ml or less of the monoclonal antihTSLPR antibody or purified isotype controls, at ambient temperature for one to two hours. The wells can then be reacted with either human IgG1 or human IgM-specific alkaline phosphatase-conjugated probes. Plates are then developed and analyzed so that the isotype bf the purified antibody can be determined.

To demonstrate binding of monoclonal anti-hTSLPR antibodies to live cells expressing an hTSLPR polypeptide, flow cytometry can be used. Briefly, cell lines expressing hTSLPR (grown under standard growth conditions) can be mixed with various concentrations of an anti-hTSLPR antibody in PBS containing 0.1% BSA and 100% fetal calf serum, and incubated at 37° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-hTSLPR antibodies of the invention can be further tested for reactivity with an hTSLPR polypeptide or antigenic fragment by Western blotting. Briefly, purified hTSLPR polypeptides or fusion proteins, or cell extracts from cells expressing TSLPR can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

V. NON-IMMUNOGLOBULIN SCAFFOLDS

A wide variety of antibody/immunoglobulin frameworks or scaffolds can be employed so long as the resulting polypeptide includes at least one binding region which is specific for the target protein. Such frameworks or scaffolds include the 5 main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target protein of SEQ ID NO. X. Such compounds are known herein as "polypeptides comprising a target-specific binding region". Known non-immunoglobulin frameworks or scaffolds include, but are not limited to, Adnectins (fibronectin) (Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (Pieris Proteolab AG, Freising, Germany), small modular immuno-pharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (Scil Proteins GmbH, Halle, Germany).

(i) Adnectins—Compound Therapeutics

The adnectin scaffolds are based on fibronectin type III domain (e.g., the tenth module of the fibronectin type III (10 Fn3 domain). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands. (U.S. Pat. No. 6,818,418).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

(ii) Ankyrin—Molecular Partners

The technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

(iii) Maxybodies/Avimers—Avidia

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, 20040175756; 20050053973; 20050048512; and 20060008844.

(vi) Protein A—Affibody

Affibody® affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate Affibody® libraries with a large number of ligand variants (See e.g., U.S. Pat. No. 5,831,012). Affibody® molecules mimic antibodies, they have a molecular weight of 6 kDa, compared to the molecular weight of antibodies, which is 150 kDa. In spite of its small size, the binding site of Affibody® molecules is similar to that of an antibody.

(v) Anticalins—*Pieris*

Anticalins® are products developed by the company *Pieris* ProteoLab AG. They are derived from lipocalins, a widespread group of small and robust proteins that are usually involved in the physiological transport or storage of chemically sensitive or insoluble compounds. Several natural lipocalins occur in human tissues or body liquids.

The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain.

The set of four loops, which makes up the binding pocket, shows pronounced structural plasticity and tolerates a variety of side chains. The binding site can thus be reshaped in a proprietary process in order to recognize prescribed target molecules of different shape with high affinity and specificity.

One protein of lipocalin family, the bilin-binding protein (BBP) of *Pieris Brassicae* has been used to develop anticalins by mutagenizing the set of four loops. One example of a patent application describing "anticalins" is PCT WO 199916873.

(vi) Affilin—Scil Proteins

Affilin™ molecules are small non-immunoglobulin proteins which are designed for specific affinities towards proteins and small molecules. New Affilimm molecules can be very quickly selected from two libraries, each of which is based on a different human derived scaffold protein. Affilin™ molecules do not show any structural homology to immunoglobulin proteins. Scil Proteins employs two Affilin™ scaffolds, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

VI. THERAPEUTIC APPLICATIONS OF THE ANTI-HTSLPR ANTIBODIES

The anti-hTSLPR antibodies can be employed in many therapeutic or prophylactic applications by inhibiting TSLP signaling activities. These include treating diseases or conditions mediated by TSLP singaling, such as those affecting B-cell development, T-cell development, T-cell receptor gene rearrangement, or regulation of the Stat5 transcription factor. For example, the anti-hTSLPR antagonist antibodies can be employed to suppress or reduce undesired immune response mediated by $T_H2$ cell. In particular, they are suitable for treating human patients suffering from allergic inflammatory disorders associated with or mediated by TSLP signaling. Allergic inflammatory diseases that are amenable to treatment with the anti-hTSLPR antibodies of the invention include, e.g., (1) asthma, a chronic inflammatory disease of the airways associated with airflow obstruction and bronchial hyper-responsiveness; (2) atopic dermatitis, a chronic, exacerbating inflammatory skin disease requiring long-term intermittent treatment; and (3) allergic rhinitis, an inflammatory disorder of the nasal mucosa, mediated by $T_H2$ lymphocytes which are linked to atopy. In the U.S. and several major European countries, the diagnosed prevalence for asthma, atopic dermatitis and allergic rhinitis is expected to increase from 46 million at present to 53 million, from 31.7 million at present to 37.2 million, and from 55.9 million at present to 64.5 million in 2013, respectively. About 50 to 80 percent of patients with atopic dermatitis have or will develop asthma or allergic rhinitis.

Most drugs currently available for treating allergies are aimed at providing symptomatic relief while there is relatively little effort in the immunomodulation field likely to provide long term disease modification. The anti-hTSLPR antibodies of the invention can provide novel and effective treatment of subjects (esp., human patients) suffering from any of these allergic diseases. By preventing TSLP from activating the TSLP receptor signal transduction pathway, they can block the $T_H2$ response and the production of cytokines responsible for both initiation and maintenance of allergic inflammation. Hence this approach has the potential to induce a long term therapeutic effect and disease modifying benefit in patients with atopic dermatitis, asthma and allergic rhinitis.

In another embodiment, the invention provides a pharmaceutical composition having at least one of any of the above antibodies or functional fragments or conservative variants, and a pharmaceutically acceptable carrier or excipient therefor.

In certain embodiments, the invention provides a method for treating a disorder or condition associated with the presence of a cell having a receptor target hTSLP. The method involves administering to a subject in need thereof an effective amount of any of the above pharmaceutical compositions. In a related embodiment, the disorder or condition to be treated is a respiratory disorder.

In another embodiment, the disorder or condition to be treated is bronchial asthma, which is a common persistent inflammatory disease of the lung characterised by airways hyper-responsiveness (AHR), mucus overproduction, fibrosis and raised serum IgE levels.

In another embodiment, the disorder or condition to be treated is atopic (allergic) dermatitis, which is the most common skin disease in childhood and is characterized by intense pruritus and chronic eczematous plaques.

In another embodiment, the disorder or condition to be treated is selected from other inflammatory or obstructive airways diseases and conditions such as COPD, acute lung injury (ALI), acute/adult respiratory distress syndrome (ARDS), dyspnea, allergic airway inflammation, small airway disease, lung carcinoma, acute chest syndrome in patients with sickle cell disease and pulmonary hypertension, as well as exacerbation of airways hyperreactivity consequent to other drug therapy, in particular other inhaled drug therapy.

In another embodiment, the disorder or condition to be treated is bronchitis of whatever type or genesis including, e.g., acute, arachidic, catarrhal, croupus, chronic or phthinoid bronchitis.

In another embodiment, the disorder or condition to be treated includes pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

In another embodiment, the disorder or condition to be treated is selected from atopic rhinitis (hay fever) and chronic sinusitis.

In another embodiment, the disorder or condition to be treated is selected from other inflammatory conditions of the skin, for example, psoriasis or lupus erythematosus.

In another embodiment, the disorder or condition to be treated is inflammatory bowel disease, such as ulcerative colitis and Crohn's disease.

In another embodiment, the disorder or condition to be treated is selected from other fibrotic conditions, such as systemic scelrosis, liver fibrosis, pulmonary fibrosis, idiopathic pulmonary fibrosis or fibroid lung.

In another embodiment, the disorder or condition to be treated is tumour recurrence or metastasis. Inhibition of Th2 cytokines has been shown to enhance anti-viral vaccines in animal models and may be beneficial in the treatment of HIV and other infectious diseases [Ahlers, J. D., et al. Proc Natl Acad Sci USA, 2002].

In another embodiment, the disorder or condition to be treated is a respiratory viral infection, which exacerbates underlying chronic conditions such as asthma, chronic bronchitis; COPD, otitis media, and sinusitis. The respiratory viral infection treated may be associated with secondary bacterial infection, such as otitis media, sinusitis or pneumonia.

In another embodiment, the disorder or condition to be treated is selected from other diseases or conditions, in particular diseases or conditions having an inflammatory component, for example, diseases of the bone and joints including rheumatoid arthritis, psoriatic arthritis, and other diseases such as atherosclerosis, multiple sclerosis, and acute and chronic allograft rejection, e.g. following transplantation of heart, kidney, liver, lung or bone marrow.

In another embodiment, the disorder or condition to be treated is endotoxic shock, glomerulonephritis, cerebral and cardiac ischemia, Alzheimer's disease, cystic fibrosis, virus infections and the exacerbations associated with them, acquired immune deficiency syndrome (AIDS), multiple sclerosis (MS), *Helicobacter pylori* associated gastritis, and cancers, particularly the growth of ovarian cancer.

In another embodiment, the disorder or condition to be treated is the symptoms caused by viral infection in a human which is caused by the human rhinovirus, other enterovirus, coronavirus, herpes viruses, influenza virus, parainfluenza virus, respiratory syncytial virus or an adenovirus.

Treatment in accordance with the present invention may be symptomatic or prophylactic.

The effectiveness of an agent of the invention in inhibiting inflammatory conditions, for example in inflammatory airways diseases, may be demonstrated in an animal model, e.g. mouse, rat or rabbit model, of airway inflammation or other inflammatory conditions, for example as described by Wada et al, *J. Exp. Med.* (1994) 180:1135-40; Sekido et al, *Nature* (1993) 365:654-57; Modelska et al., *Am. J. Respir. Crit. Care. Med.* (1999) 160:1450-56; and Laffon et al (1999) *Am. J. Respir. Crit. Care Med.* 160:1443-49.

In yet another embodiment, the invention provides a method for identifying a cell having a hTSLP receptor. This method involves contacting the cell with any of the above antibodies or antibody fragments further having a detectable label. The label is radioactive, fluorescent, magnetic, paramagnetic, or chemiluminescent. The method further can involve any of the above imaging or separating the labeled cell.

In another embodiment, any of the above human or humanized antibodies or antibody fragments are synthetic.

In another embodiment, the invention provides a pharmaceutical composition and an additional therapeutic agent.

The additional therapeutic agent can be selected from the group consisting of anti-inflammatory, bronchodilatory, antihistamine or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. A therapeutic agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone-furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTB4 antagonists such as BIIL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700; LTD4 antagonists such include montelukast, pranlukast, zafirlukast, accolate, SR2640, Wy-48,252, ICI 198615, MK-571, LY-171883, Ro 24-5913 and L-648051; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfanna), PD189659/PD168787 (Parke-Davis), AWD-12-281 (Asta Medica), CDC-801 (Celgene), SeICID(TM) CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; $A_{2A}$ agonists such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, and WO 03/086408; and $A_{2B}$ antagonists such as those described in WO 02/42298.

Suitable bronchodilatory drugs include anticholinergic or antimuscarinic agents, in particular ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285; and beta-2 adrenoceptor agonists such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula I of WO 00/75114, which document is incorporated herein by reference, preferably compounds of the Examples thereof, especially the compound (5-[(R)-2-(5,6-Diethyl-indan-2-ylamino)-1-hydroxy-ethyl]-8-hydroxy-11H-quinolin-2-one) and pharmaceutically acceptable salts thereof, as well as compounds (in free or salt or solvate form) of formula I of WO 04/16601, and also compounds of EP 1440966, JP 05025045, WO 93/18007, WO 99/64035, US 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, EP1460064, WO 04/087142, WO 04/089892, EP 01477167, US 2004/0242622, US 2004/0229904, WO 04/108675, WO 04/108676, WO 05/033121, WO 05/040103 and WO 05/044787.

Suitable dual anti-inflammatory and bronchodilatory drugs include dual beta-2 adrenoceptor agonist/muscarinic antagonists such as those disclosed in US 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in JP 2004107299, WO 03/099807 and WO 04/026841.

Combinations of therapeutic agents of the invention and anticholinergic or antimuscarinic agents, steroids, beta-2 agonists, PDE4 inhibitors, dopamine receptor agonists, LTD4 antagonists or LTB4 antagonists may also be used. Other useful combinations of agents of the invention with anti-inflammatory drugs are those with other antagonists of chemokine receptors, e.g. CCR-1, CCR-3, CCR4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]-tetrahydro-N,N-dimethyl-2H-pyran-4-aminium chloride (TAK-770), CCR-5 antagonists described in U.S. Pat. No. 6,166,037 (particularly claims 18 and 19), WO 0066558 (particularly claim 8), WO 0066559 (particularly claim 9), WO 04/018425 and WO 04/026873.

The additional therapeutic agent may also be selected from the group consisting of other cytokine binding molecules, particularly antibodies of other cytokines, in particular a combination with an anti-IL4 antibody, such as described in PCT/EP2005/00836, an anti-IgE antibody, such as Xolair®, an anti-IL31 antibody, an anti-IL31R antibody, an anti-IL13 antibody, such as described in WO05/007699, an anti-endoglin antibody, an anti-IL1b antibody, an anti-TSLP antibody or another anti-hTSLPR antibody.

The anti-hTSLPR antagonist antibodies of the invention can be employed to treat a subject both therapeutically and prophylactically. In therapeutic applications, a composition comprising an anti-hTSLPR antagonist antibody (e.g., a humanized anti-hTSLPR antibody) is administered to a subject already affected by an allergic disease caused by or associated with TSLP signaling. The composition contains the antibody in an amount sufficient to cure, partially arrest, or detectably slow the progression of the condition, and its complications. In prophylactic applications, compositions containing the monoclonal anti-hTSLPR antibodies are administered to a patient not already suffering from an allergic inflammatory disorder. Rather, they are directed to a subject who are at the risk of, or has a predisposition, to developing an allergic inflammatory disorder. Such applications allow the subject to enhance the patient's resistance or to retard the progression of an allergic inflammatory disorder mediated by TSLP signaling.

VII. PHARMACEUTICAL COMPOSITIONS

The invention provides pharmaceutical compositions comprising the anti-hTSLPR monoclonal antibodies (intact or binding fragments) formulated together with a pharmaceutically acceptable carrier. The compositions can additionally contain other therapeutica agents that are suitable for treating or preventing a given allergic disorder, e.g., the known anti-allergy agents noted above. Pharmaceutically carriers enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Typically, a therapeutically effective dose or efficacious dose of the anti-hTSLPR antibody is employed in the pharmaceutical compositions of the invention. The anti-hTSLPR antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies of the invention employed in the pharmaceutical composition at levels lower than that required to achieve the desired therapeutic effect and gradually increase the dosage until the desired effect is achieved. In general, effective doses of the compositions of the present invention, for the treatment of an allergic inflammatory disorder described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months.

Antibody is usually administered on multiple occasions. Intervals between single dosages can be weekly, monthly or yearly. Intervals can also be irregular as indicated by measuring blood levels of anti-hTSLPR antibody in the patient. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

EXAMPLES

The following examples are provided to further illustrate the invention but not to limit its scope. Other variants of the invention will be readily apparent to one of ordinary skill in the art and are encompassed by the appended claims.

Example 1

Development of a Mouse Anti-hTSLPR Antagonist Antibody

This Example describes the development of a mouse anti-hTSLPR antagonist antibody. Bcl2 Wehi22 mouse (#1770) was immunized with human TSLPR (Met 1-Lys 231)/human IgG1 Fc (Pro 100-Lys 330) fusion protein purchased from R&D System (Minneapolis, Minn.) (Cat. No. 981-TR, Lot No. EDY1312A). The immunization was carried out in total 8 times of injections over 18 days. B-cells were isolated from peripheral lymph nodes and fused to F0 myeloma cells (ATCC, Manassas, Va.). Antibody production was screened by ELISA against hTSLPR/Fc protein. A total of 24 clones were obtained which produce antibodies that specifically recognize hTSLPR. Binding of hTSLPR antibodies to cell surface TSLPR was analyzed in FACS assay (BD Biosciences, San Jose, Calif.). Briefly, BaF3/hTSLPR/hIL7Rα cells, were incubated with hybridoma culture supernatants followed by FITC-conjugated anti-mouse IgG, and analyzed on a FACS machine. The results showed that 14 hybridoma clones out of 24 clones were able to bind to the cell surface receptor.

An hTSLP-dependent cell proliferation assay in BaF3/hTSLPR/hIL7Rα cells was then employed to screen for hTSLPR antagonist antibodies. The cells express both human TSLPR and IL7Rα, and are able to respond to stimulation of human TSLP (Reche et al., J. Immunol., 167:336-43, 2001). The cell proliferation assay was performed essentially as described in Reche et al. Briefly, BaF3/hTSLPR/hIL7Rα cells were pre-incubated with antibodies from cultured supernatants for 1 hour, and induced with hTSLP at indicated concentrations indicated in FIG. 1. Cell proliferation was measured using Alamar Blue (TREK Diagnositc Systems, Cleveland, Ohio). For each parental clone, one to three subclones were used in the assay. The results, as showm in FIG. 1, indicate that three subclones from clone 1D6 showed strong antagonist activity.

Figure 2:
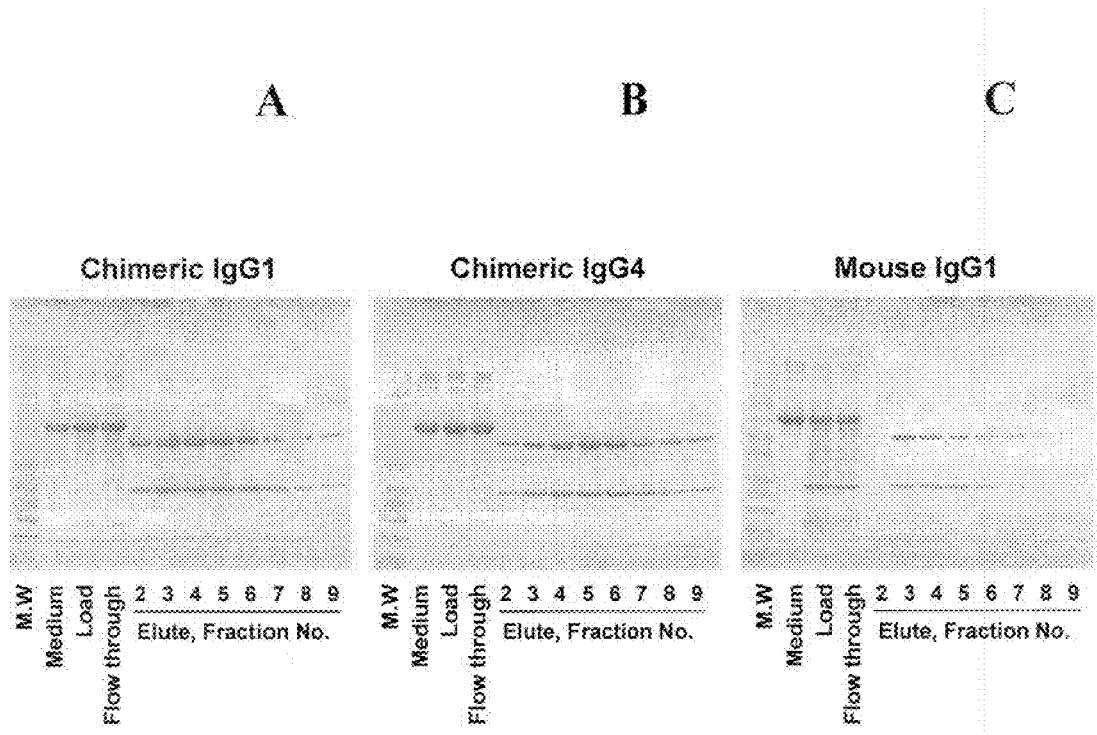
FIGS. 2A-2C show purification of mouse and chimeric anti-hTSLPR monoclonal antibodies. A: chimeric IgG1 antibody; B: chimeric IgG4 antibody; and C: mouse IgG1 antibody.
Figure 3:
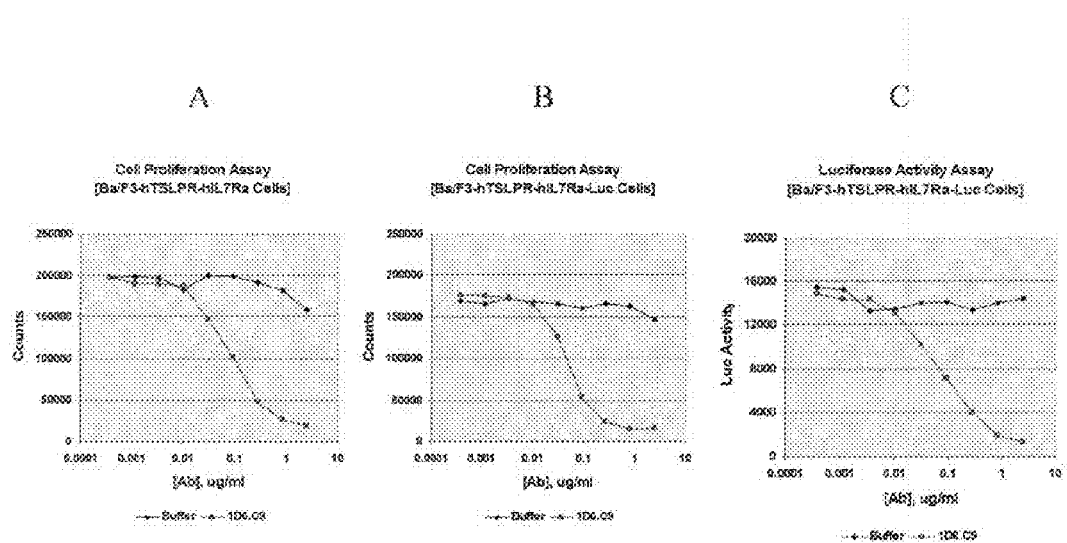
FIGS. 3A-3C show antagonist activity of purified mouse anti hTSLPR antibody (clone 1D6.C9) by cell proliferation assay and luciferase reporter assay. A: proliferation of Ba/F3-hTSLPR-hIL7Rα cells; B: proliferation of BaF3/hTSLPR/hIL7Rα/Stat5-Luc cells; and C: luciferase activity of BaF3/hTSLPR/hIL7Rα/Stat5-Luc cells.

Monoclonal antibody (mAb) from one of the subclones, 1D6.C9, was purified (FIG. 2C). Briefly, serum-free conditioned medium from Miniperm culture (Vivascience, Carlsbad, Calif.) was treated with Cleanascite (LigoChem, Fairfield, N.J.). Antibody was then purified over Protein G resin (Amersham Biosciences, Piscataway, N.J.). The purified antibody was tested in the cell proliferation assay as described above. Ba/F3-hTSLPR-hIL7Rα cells or Baf3/hTSLPR/hIL7Rα/Stat5-Lue cells were treated with different concentrations of the antibody for 1 hour prior to addition of 1 ng/ml hTSLP. The results indicate that TSLP-dependent proliferation of both BaF3/hTSLPR/hIL7Rα; cells (FIG. 3A) and Baf3/hTSLPR/hIL7Rα/Stat5-Luc cells (FIG. 3B) was inhibited by the addition of the mouse anti-hTSLPR antibody in a dose-dependent manner.

In addition, a luciferase reporter assay was also employed to examine the effect of the antibody on TSLP-mediated signaling activities. TSLP induces phosphorylation of Stat3 and Stat5 in Baf3/hTSLPR/hIL7Ra cells (Reche et al., supra). This assay was designed to measure reporter gene expression under the control of Stat5 in the Baf3/hTSLPR/hIL7Ra/Stat5-Luc cells in response to TSLP signaling. Briefly, the Stat-Lue reporter construct was generated by inserting a Stat consensus binding site into a pGL2 basic Luc reporter vector (Promega, Madison, Wis.) that does not contain promoter and enhancer. The inserted Stat binding site contains 8 copies of a GATTTCCCCGAAATG sequence element (SEQ ID NO: 15) which harbors the core Stat binding sequence of TTC-CCGGAA (SEQ ID NO: 16) (Yan et al., Cell. 84:421-30, 1996; and Saylors et al., Gene Ther. 6:944-6, 1999). The Stat-Luc reporter construct was introduced into the BaF3/hTSLPR/hIL7Rα cells. The resulting BaF3/hTSLPR/hIL7Rα/Stat5-Luc cells were treated with different concentrations of the mouse antibody for 1 hour prior to addition of 1 ng/ml of hTSLP. Luciferase activity was measured using Bright Glo (Promega, Madison, Wis.). Results obtained from the assay were shown in FIG. 3C. Similar to results from the cell proliferation assay, data from the Stat5-Luc reporter assay also demonstrated the dose-dependent antagonist activity of the mouse anti-hTSLPR antibody.

Variable regions of mAb 1D6.C9 heavy chain (VE) and light chain (VL) were cloned out by RT-PCR. Sequences of the primers used for identification of variable regions of the heavy and light chains are as follows. Primers for VH are: (1) VH9: GATGGCAGCWGCYCAAAG (SEQ ID NO: 1); and (2) H-Constant: GCGTCTAGAAYCTCCACACACAGGR-RCCAGTGGATAGAC (SEQ ID NO: 2). Primers for VL are: (1) LCV3: GGGTCTAGACACCATGGAGWCACAKWCT-CAGGTCTTTRTA (SEQ ID NO: 3); and L-Constant: GCGTCTAGAACTGGATGGTGGGAAGATGG (SEQ ID NO: 4).

In brief, total RNA was isolated from 1D6.C9 clone. RT-PCR was carried out with forward primers against signal sequence of either heavy or light chain variable regions, and reverse primers against heavy chain CH1 region or light chain kappa constant region. PCR products were cloned into pCR II orpcDNA3.1/V5-His-TPOP-TA vector for sequencing. Polynucleotide sequences of the heavy chain and light chain variable region sequences of this antibody clone were then determined (FIG. 4). The corresponding amino acid sequences of the variable regions (SEQ ID NO: 5 and SEQ ID NO: 6) are shown in FIG. 5. Also indicated in FIG. 5 are the CDR regions and the framework regions deduced in accordance with the numbering system of Kabat et al., supra.

Example 2

Generation of Chimeric Anti-hTSLPA Antibodies

This Example describes the generation and characterization of chimeric anti-hTSLPR antibodies. The chimeric antibodies contain variable regions from the above noted mouse anti-hTSLPR antibody 1D6.C9 clone and constant regions from human immuglobulins.

To generate the chimeric antibodies, the variable regions of the mouse antibody against human TSLPR clone 1D6.C9 were prepared using PCR techniques and primer sequences described in Example 1 designed for cloning into cassette vectors. The PCR products were then respectively cloned into cassette vectors which contain in-frame fusions with human immunoglobulin leader sequences, J-segments and splicer-donor signals using the sequences shown in Table 1. The sequences were then transferred into mammalian expression vectors containing human immunoglobulin constant region, e.g. SP2/0 vectors.

TABLE 1

Primers sequences for cloning into IgG1 kappa expression vectors

| Primers | Sequences |
|---|---|
| NV115-3B-VH for | 5' phosphorylated CAGGCCCAGGTCCAGCTGGTGCAG SEQ ID NO: 18 |
| NV115-3B-VH rev | GGAGCTCACGGTCACCAGGG SEQ ID NO: 19 |
| NV115-3B-VK for | GAGTACGCGTTGTGACATCCAGATGACCCAG SEQ ID NO: 20 |
| NV115-3B-VK-rev | GCTCAAGCTTCGTACCTTGGCCAAACG SEQ ID NO: 21 |

Selection for clones expressing the heavy chain were based on neomycin selection, while clones expressing the light chain were selected using dhfr selection. Gene amplification was initiated using methotrexate. The variable region cassette for heavy chain was transferred to human IgG1 and IgG4 mammalian expression vectors, respectively.

Figure 6:
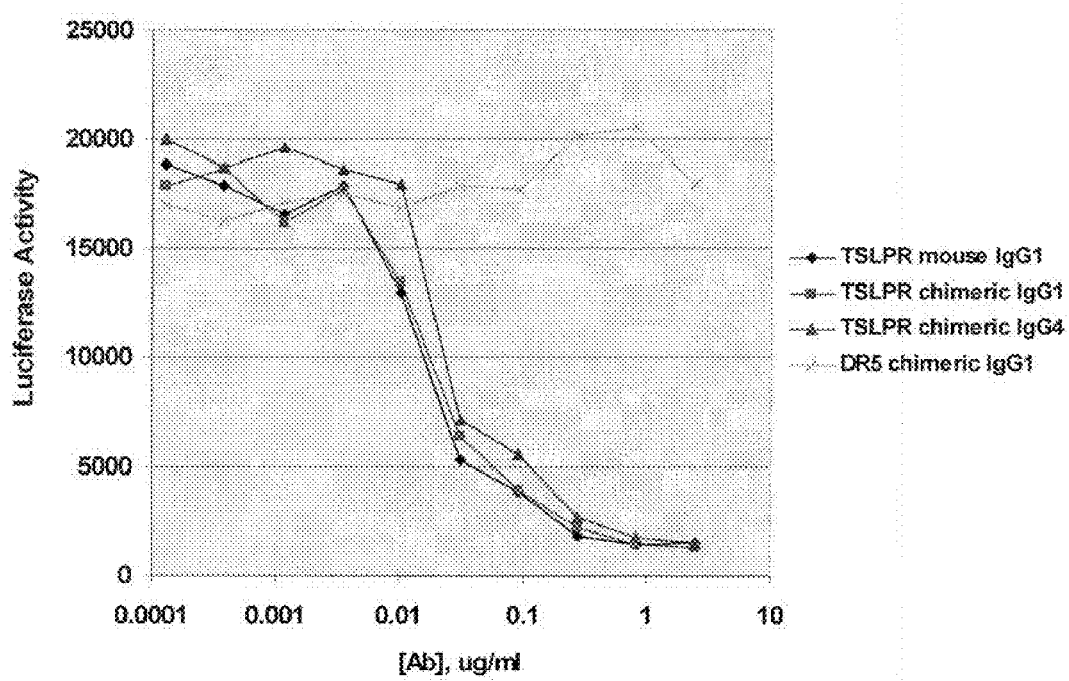
FIG. 6 shows results from luciferase reporter assays comparing antagonist activity of purified mouse and chimeric anti-hTSLPR antibodies in Ba/F3 cells overexpressing hTSLPR, hIL7Rα, and Stat5-Luc.

Following the subcloning, to produce IgG1 chimeric antibodies, DNA plasmids of chimeric IgG1 heavy chain and kappa light chain were co-electroporated into SP2/0 myeloma cells. Likewise, to produce IgG4 chimeric antibodies, and chimeric IgG4 heavy chain and kappa light chain were co-electroporated into SP2/0 myeloma cells. The cells were selected with geneticin, and then cultured and expand in growth medium containing geneticine and methotrexate. Cells were adapted into serum-free medium for antibody purification. Chimeric IgG1 and IgG4 antibodies secreted from transfected SP2/0 cells were purified (FIG. 2A and FIG. 2B). Antagonist activity of the purified chimeric IgG1 and IgG4 antibodies was compared to that of the mouse antibody in the Luc reporter assay. An IgG1 chimeric antibody against death receptor 5 (DR5) was used as negative control. As measured by reporter gene expression in Ba/F3 cells overexpressing hTSLPR, hIL7Rα, and Stat5-Luc, the results indicate that the chimeric anti-hTSLPR antibodies exhibited similar antagonist activity as that of the mouse IgG1 antibody (FIG. 6).

Example 3

Anti-hTSLPR Antibody Inhibits TSLP-Mediated TARC Secretion

Figure 7:
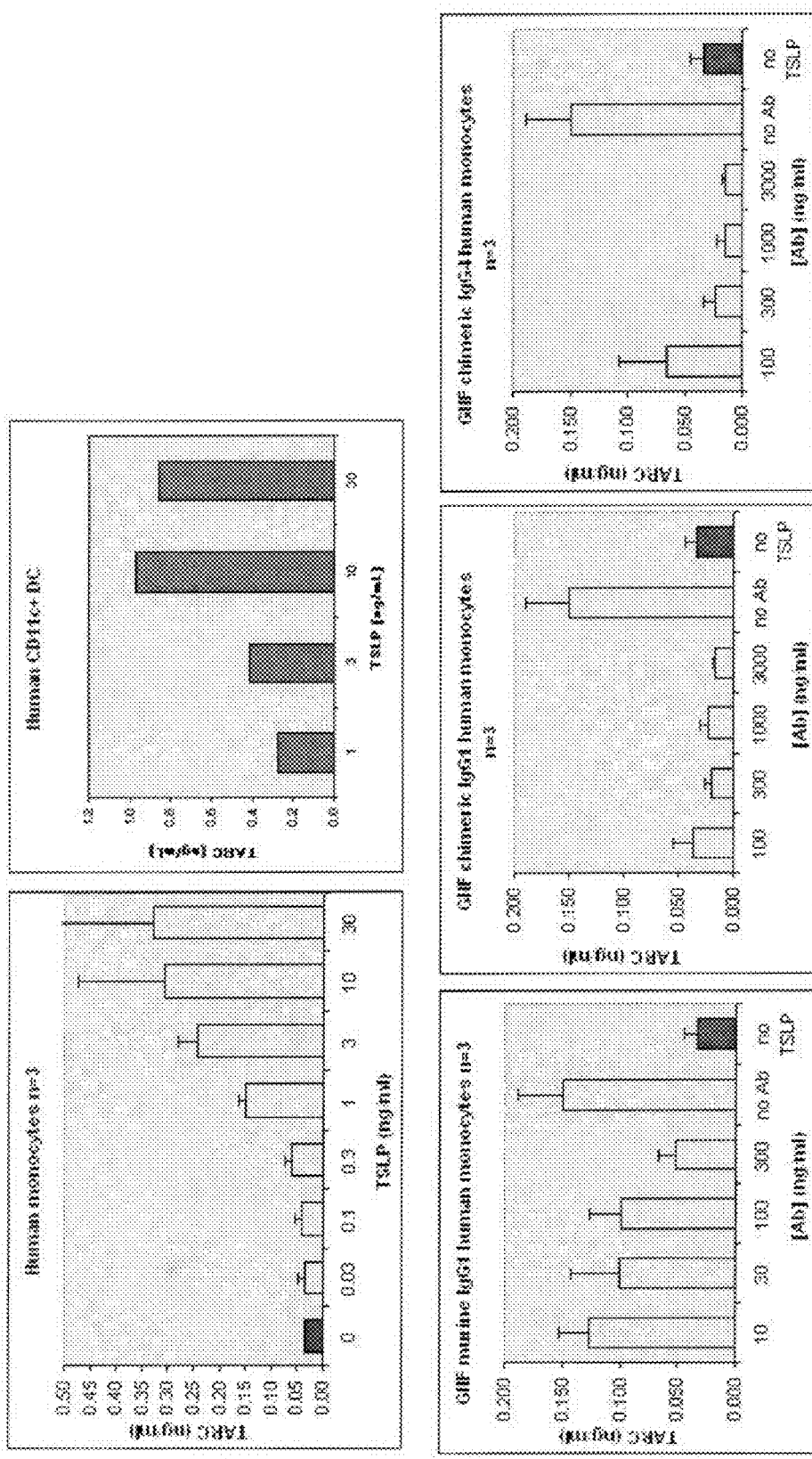
FIG. 7 shows inhibition of TSLP-mediated TARC section from human monocytes by the mouse and chimeric anti-hTSLPR antibodies.

This Example describes inhibition of TSLP-mediated TARC section from human monocytes by the anti-hTSLPR antagonist antibodies. Both the mouse and the chimeric anti-hTSLPR antibodies noted above were examined for effect on TSLP-mediated secretion of the $T_H2$-attracting thymus and activation-regulated chemokine (TARC) by human monocytes. Except for the addition of the anti-hTSLPR antibodies, the TARC secretion assays were performed essentially as described in Soumelis et al., Nat Immunol. 3:673-80, 2002. The results are shown in FIG. 7. The top two panels of the figure respectively show TARKC section from human monocytes and CD11+ dendritic cells stimulated with TSLP. The bottom three panels respectively show the effect of three different anti-hTSLPR antibodies on TSLP-mediated TARC section from human monocytes. As demonstrated in the figure, the mouse anti-hTSLPR antibody and the chimeric anti-hTSLPR antibodies (both IgG1 and IgG4 isotypes) were all able to inhibit TARC secretion from human monocytes in a dose dependent manner. This further validated the antagonizing activity of the anti-hTSLPR antibodies on TSLP signaling.

Binding studies to determine binding affinities of anti-hTSLPR antibodies were conducted using standard Biacore plasmon resonance analysis to measure "on" (ka) and "off" (kd) rates. These measurements lead to the calculation of binding contant (KD) for the antibody. Further analysis was also conducted using ForteBiop to examine solution binding kinetics. In addition, cellular assay were used to determine the IC50 for the antibody. thes results of these studies are summarized in Table 3.

TABLE 3

Affinity, biological activity, specificity and cyno reactivity data for target antibody

| Antibody | Affinity | | Biological Activity | | | | | Specificity | Reactivity |
|---|---|---|---|---|---|---|---|---|---|
| | Biaocre KD [pM] Human TSLPR | Forte KD [pM] Human TSLPR | IC50 [pM] Human TSLPR RGA (15% Serum) | IC50 [pM] Human TSLPR (15% serum) | IC50 [pM] Human TSLPR Prolif. | IC50 [pM] Human TSLPR Prolif. (15% serum) | IC50 [pM] Human TSLPR Monocyte | IL-&Ra Reactivity % h TSLPR binding | Cyno Reactivity % hTSLPR binding |
| NV115-3B (Fab) | 101 | 51 | 270 | 950 | 210 | 200 | — | 0 | 93 |
| Target | <200 | <200 | 200 | N/A | 200 | N/A | 200 | 0 | Equivalent |

Antibody Sequences

NV115-3B Sequence
VH
QVQLVQSGAEVKKPGASVKVSCKASGYTFT<u>TYGIS</u>WLRQAPGQGLEWMG<u>W VNTNTGNPRYAQGFTG</u>RFVFSLDTSVSTAYLQISSLKAEDTAVYYCAR<u>EG FITTVVGAAGRFVY</u>WGQGTLVTVSS
(SEQ ID NO: 22)

VK
DIQMTQSPSSLSASVGDRVTITC<u>RASQDIHTRLA</u>WYQQKPGQPPKLLIY<u>W

ASTRAS</u>GVPDRFSGTGSGTDFTLTISSLQAEDVAVYYC<u>QQYSTYPT</u>FGQG

TKLEIK
(SEQ ID NO: 23)

NV115-3E Sequence
VH
QVQLVQSGAEVKKPGASVKVSCKASGYTFT<u>TYGIS</u>WLRQAPGQGLEWMG<u>W VNTNTGNPRYAQGFTG</u>RFVFSLDTSVSTAYLQISSLKAEDTAVYYCAR<u>EG FITTVVGAAGRFVY</u>WGQGTLVTVSS
(SEQ ID NO: 24)

VK
EIVMTQSPATLSLSPGERATLSC<u>RASQSVSSSLA</u>WYQQKPGQPPKLLIH<u>W

AVTRVS</u>GVPDRFSGSGSGTDFTLTISSLQAEDVAVYYC<u>QQYSTYPT</u>FGQG
TKLEIK
(SEQ ID NO: 25)

NV115-3E Sequence
VH
QVQLVQSGAEVKKPGASVKVSCKASGYTFT<u>TYGIS</u>WLRQAPGQGLEWMG<u>W VNTNTGNPRYAQGFTG</u>RFVFSLDTSVSTAYLQISSLKAEDTAVYYCAR<u>EG FITTVVGAAGRFVY</u>WGQGTLVTVSS
(SEQ ID NO: 26)

VK
DIQMTQSPSSLSASVGDRVTITC<u>RASQDIHTRLA</u>WYQQKPGQPPKLLIY<u>W

ASTRGS</u>GVPDRFSGSGSGTDFTLTISSLRAEDVAVYYC<u>QQYSTYPT</u>FGQG

TKLEIK
(SEQ ID NO: 27)

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, Genbank sequences, patents, and patent applications cited in this specification are herein incorporated by reference as if each was specifically and individually indicated to be incorporated by reference.

The invention claimed is:

1. An isolated antibody or antigen binding portion thereof comprising a heavy chain variable region comprising the sequence of amino acids 10 to 134 of SEQ ID NO: 5, wherein the isolated antibody or antigen binding portion thereof binds specifically to human thymic stromal lymphopoietin receptor.

2. The isolated antibody or antigen binding portion thereof of claim 1, which is monoclonal.

3. The isolated antibody or antigen binding portion thereof of claim 1, further comprising a light chain variable region comprising the sequence of amino acids 21 to 128 of SEQ ID NO: 6.

4. The isolated antibody or antigen binding portion thereof of claim 3, which is monoclonal.

5. An isolated antibody or antigen binding portion thereof which comprises heavy chain CDR1, CDR2 and CDR3 sequences comprising the sequences of SEQ ID NO: 7, SEQ ID NO:8 and SEQ ID NO:9, respectively, and light chain CDR1, CDR2 and CDR3 sequences comprising the sequences of SEQ ID NO: 10, SEQ ID NO: 11 and SEQ ID NO: 12, respectively, wherein the isolated antibody or antigen binding portion thereof binds specifically to human thymic stromal lymphopoietin receptor.

6. The isolated antibody or antigen binding portion thereof of claim 5 which is a mouse antibody.

7. The isolated antibody or antigen binding portion thereof of claim 5 which is a chimeric antibody.

8. The isolated antibody or antigen binding portion thereof of claim 5 which comprises a human heavy chain constant region and a human light chain constant region.

9. The isolated antibody or antigen binding portion thereof of claim 5 which is humanized.

10. The isolated antibody or antigen binding portion thereof of claim 5 which is a humanized antibody.

11. The isolated antibody or antigen binding portion thereof of claim 5 which is a single chain antibody or antigen binding portion thereof.

12. The isolated antibody or antigen binding portion thereof of claim 5 which is a Fab fragment.

13. The isolated antibody or antigen binding portion thereof of claim 5 which is of the IgG1 or IgG4 isotype.

14. The isolated antibody or antigen binding portion thereof of claim 5, which is monoclonal.

* * * * *

SEQUENCE LISTING

<160> NUMBER OF SEQ ID NOS: 28

<210> SEQ ID NO 1
<211> LENGTH: 18
<212> TYPE: DNA
<213> ORGANISM: Artificial
<220> FEATURE:
<223> OTHER INFORMATION: Primer

<400> SEQUENCE: 1
gatggcagcw gcycaaag                                                18

<210> SEQ ID NO 2
<211> LENGTH: 39
<212> TYPE: DNA
<213> ORGANISM: Artificial
<220> FEATURE:
<223> OTHER INFORMATION: Primer

<400> SEQUENCE: 2
gcgtctagaa yctccacaca caggrrccag tggatagac                    39

<210> SEQ ID NO 3
<211> LENGTH: 40
<212> TYPE: DNA
<213> ORGANISM: Artificial
<220> FEATURE:
<223> OTHER INFORMATION: Primer

<400> SEQUENCE: 3
gggtctagac accatggagw cacakwctca ggtctttrta                    40

<210> SEQ ID NO 4
<211> LENGTH: 29
<212> TYPE: DNA
<213> ORGANISM: Artificial
<220> FEATURE:
<223> OTHER INFORMATION: Primer

<400> SEQUENCE: 4
gcgtctagaa ctggatggtg ggaagatgg                                29

<210> SEQ ID NO 5
<211> LENGTH: 134
<212> TYPE: PRT
<213> ORGANISM: Artificial
<220> FEATURE:
<223> OTHER INFORMATION: Heavy chain variable domain

<400> SEQUENCE: 5

Met Ala Ala Gln Ser Ala Gln Ala Gln Ile Gln Leu Gly Gln Ser
1               5                   10                  15

Gly Pro Glu Leu Lys Lys Pro Gly Glu Thr Val Lys Ile Ser Cys Lys
            20                  25                  30

Ala Ser Gly Tyr Thr Phe Thr Thr Tyr Gly Met Ser Trp Val Lys Gln
        35                  40                  45

Ala Pro Gly Lys Gly Leu Gln Trp Met Gly Trp Ile Asn Thr Tyr Ser
    50                  55                  60

Gly Val Pro Arg Tyr Ala Asp Asp Phe Lys Gly Arg Phe Ala Phe Ser
65                  70                  75                  80

Leu Glu Thr Ser Ala Ser Thr Ala Tyr Leu Gln Ile Tyr Asn Leu Lys
                85                  90                  95

Asn Glu Asp Thr Ala Thr Tyr Phe Cys Thr Arg Glu Gly Phe Ile Thr
            100                 105                 110

Thr Val Val Gly Ala Ala Gly Arg Phe Val Tyr Trp Gly Gln Gly Thr
        115                 120                 125

Leu Val Thr Val Ser Ala
    130

<210> SEQ ID NO 6
<211> LENGTH: 128
<212> TYPE: PRT
<213> ORGANISM: Artificial
<220> FEATURE:
<223> OTHER INFORMATION: Light chain variable domain

<400> SEQUENCE: 6

Met Glu Ser His Thr Gln Val Phe Val Tyr Met Leu Leu Trp Leu Ser
1               5                   10                  15

Gly Val Glu Gly Asp Ile Val Met Thr Gln Ser His Lys Phe Met Ser
            20                  25                  30

```
Thr Ser Val Gly Asp Arg Val Ser Ile Thr Cys Lys Ala Ser Gln Asp
            35                  40                  45

Val Gly Thr Ala Val Ala Trp Tyr Gln Gln Lys Pro Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Leu Asn
                85                  90                  95

Asn Val Gln Ser Glu Asp Leu Ala Asp Tyr Phe Cys Gln Gln Tyr Ser
            100                 105                 110

Thr Tyr Pro Thr Phe Gly Ser Gly Thr Lys Leu Glu Leu Lys Arg Ala
            115                 120                 125

<210> SEQ ID NO 7
<211> LENGTH: 5
<212> TYPE: PRT
<213> ORGANISM: Artificial
<220> FEATURE:
<223> OTHER INFORMATION: CDR

<400> SEQUENCE: 7

Thr Tyr Gly Met Ser
1               5

<210> SEQ ID NO 8
<211> LENGTH: 17
<212> TYPE: PRT
<213> ORGANISM: Artificial
<220> FEATURE:
<223> OTHER INFORMATION: CDR

<400> SEQUENCE: 8

Trp Ile Asn Thr Tyr Ser Gly Val Pro Arg Tyr Ala Asp Asp Phe Lys
1               5                   10                  15

Gly

<210> SEQ ID NO 9
<211> LENGTH: 16
<212> TYPE: PRT
<213> ORGANISM: Artificial
<220> FEATURE:
<223> OTHER INFORMATION: CDR

<400> SEQUENCE: 9

Glu Gly Phe Ile Thr Thr Val Val Gly Ala Ala Gly Arg Phe Val Tyr
1               5                   10                  15

<210> SEQ ID NO 10
<211> LENGTH: 11
<212> TYPE: PRT
<213> ORGANISM: Artificial
<220> FEATURE:
<223> OTHER INFORMATION: CDR

<400> SEQUENCE: 10

Lys Ala Ser Gln Asp Val Gly Thr Ala Val Ala
1               5                   10

<210> SEQ ID NO 11
<211> LENGTH: 7
<212> TYPE: PRT
<213> ORGANISM: Artificial
<220> FEATURE:
<223> OTHER INFORMATION: CDR
```

```
<400> SEQUENCE: 11

Trp Ala Ser Thr Arg His Thr
1               5

<210> SEQ ID NO 12
<211> LENGTH: 8
<212> TYPE: PRT
<213> ORGANISM: Artificial
<220> FEATURE:
<223> OTHER INFORMATION: CDR

<400> SEQUENCE: 12

Gln Gln Tyr Ser Thr Tyr Pro Thr
1               5

<210> SEQ ID NO 13
<211> LENGTH: 401
<212> TYPE: DNA
<213> ORGANISM: Artificial
<220> FEATURE:
<223> OTHER INFORMATION: Hybridoma heavy chain DNA sequence

<400> SEQUENCE: 13
atggcagctg ctcaaagtgc ccaagcacag atccagttgg acagtctgg acctgagcga      60 agaagcctgg agagacagtc aagatctcct gcaaggcttc tgggtatacc ttcacaacct    120
atggaatgag ctgggtgaaa caggctccag gaaagggttt acagtggatg gctggataa    180 atacctactc tggagtgcca agatatgctg atgacttcaa gggacgattt gccttctctt   240
tggaaacctc tgccagcact gcctatctgc agatctacaa cctcaaaaat gaggacacgg   300
ctacatattt ctgtacaaga gaaggattta ttactacggt agtaggtgcg gctgggaggt   360
ttgtttattg gggccaaggg actctggtca ctgtctctgc a                        401

<210> SEQ ID NO 14
<211> LENGTH: 383
<212> TYPE: DNA
<213> ORGANISM: Artificial
<220> FEATURE:
<223> OTHER INFORMATION: Hybridoma light chain DNA sequence

<400> SEQUENCE: 14
atggagtcac atactcaggt ctttgtatac atgttgctgt ggttgtctgg tgttgaagag      60
acattgtgat gacccagtct cacaaattca tgtccacatc agtaggagac agggtcagca    120
tcacctgcaa ggccagtcag gatgtgggta ccgctgtagc ctggtatcaa cagaaaccag    180
ggcaatctcc taaactactg atttactggg catccacccg gcacactgga gtccctgatc    240
gcttcacagg cagtggatct gggacagatt tcactctcac ccttaacaat gtgcagtctg    300
aagacttggc agattatttc tgtcagcaat atagcaccta tcccacgttc ggtagtggga    360
ccaagctgga gctgaaacgg gct                                            383

<210> SEQ ID NO 15
<211> LENGTH: 15
<212> TYPE: DNA
<213> ORGANISM: Artificial
<220> FEATURE:
<223> OTHER INFORMATION: Stat element

<400> SEQUENCE: 15
gatttccccg aaatg                                                      15

<210> SEQ ID NO 16
```

```
<211> LENGTH: 9
<212> TYPE: DNA
<213> ORGANISM: Artificial
<220> FEATURE:
<223> OTHER INFORMATION: Stat element

<400> SEQUENCE: 16 ttcccggaa                                                                    9

<210> SEQ ID NO 17
<211> LENGTH: 375
<212> TYPE: DNA
<213> ORGANISM: Artificial
<220> FEATURE:
<223> OTHER INFORMATION: NV115-3B VH Genart DNA sequence

<400> SEQUENCE: 17
caggtgcagc tggtgcagag cggagccgag gtgaagaagc ctggcgccag cgtcaaggtg           60
tcctgcaagg ccagcggcta caccttcacc acctacggca tcagctggct gcggcaggcc          120
cctgggcagg gcctggaatg gatgggctgg gtgaacacca acaccggcaa ccccagatac          180
gcccagggct tcaccggccg gttcgtgttc agcctggaca ccagcgtgtc caccgcctac          240
ctgcagatca gcagcctgaa ggccgaggac accgccgtgt actactgcgc cagagagggc          300
ttcatcacca ccgtggtggg agccgccgga agattcgtgt actggggcca gggcaccctg          360
gtcaccgtct cctca                                                           375

<210> SEQ ID NO 18
<211> LENGTH: 24
<212> TYPE: DNA
<213> ORGANISM: Artificial
<220> FEATURE:
<223> OTHER INFORMATION: Primer

<400> SEQUENCE: 18
caggcccagg tccagctggt gcag                                                  24

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
ggagctcacg gtcaccaggg                                                       20

<210> SEQ ID NO 20
<211> LENGTH: 31
<212> TYPE: DNA
<213> ORGANISM: Artificial
<220> FEATURE:
<223> OTHER INFORMATION: Primer

<400> SEQUENCE: 20
gagtacgcgt tgtgacatcc agatgaccca g                                          31

<210> SEQ ID NO 21
<211> LENGTH: 27
<212> TYPE: DNA
<213> ORGANISM: Artificial
<220> FEATURE:
<223> OTHER INFORMATION: Primer

<400> SEQUENCE: 21
```
gctcaagctt cgtaccttgg ccaaacg          27

```
<210> SEQ ID NO 22
<211> LENGTH: 125
<212> TYPE: PRT
<213> ORGANISM: Artificial
<220> FEATURE:
<223> OTHER INFORMATION: Variable domain

<400> SEQUENCE: 22
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Leu Arg Gln Ala Pro Gly Gln Gly Leu Glu Trp Met
        35                  40                  45

Gly Trp Val Asn Thr Asn Thr Gly Asn Pro Arg Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Gly Phe Ile Thr Thr Val Val Gly Ala Ala Gly Arg Phe
            100                 105                 110

Val Tyr Trp Gly Gln Gly Thr Leu Val Thr Val Ser Ser
        115                 120                 125

```
<210> SEQ ID NO 23
<211> LENGTH: 106
<212> TYPE: PRT
<213> ORGANISM: Artificial
<220> FEATURE:
<223> OTHER INFORMATION: Variable domain

<400> SEQUENCE: 23
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Thr Arg
            20                  25                  30

Leu Ala Trp Tyr Gln Gln Lys Pro Gly Gln Pro Pro Lys Leu Leu Ile
        35                  40                  45

Tyr Trp Ala Ser Thr Arg Ala Ser Gly Val Pro Asp Arg Phe Ser Gly
    50                  55                  60

Thr Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Ser Tyr Pro Thr
                85                  90                  95

Phe Gly Gln Gly Thr Lys Leu Glu Ile Lys
            100                 105

```
<210> SEQ ID NO 24
<211> LENGTH: 125
<212> TYPE: PRT
<213> ORGANISM: Artificial
<220> FEATURE:
<223> OTHER INFORMATION: Variable domain

<400> SEQUENCE: 24
```

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Thr Tyr
            20                  25                  30

Gly Ile Ser Trp Leu Arg Gln Ala Pro Gly Gln Gly Leu Glu Trp Met
            35                  40                  45

Gly Trp Val Asn Thr Asn Thr Gly Asn Pro Arg Tyr Ala Gln Gly Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95

Ala Arg Glu Gly Phe Ile Thr Val Val Gly Ala Ala Gly Arg Phe
            100                 105                 110

Val Tyr Trp Gly Gln Gly Thr Leu Val Thr Val Ser Ser
            115                 120                 125

<210> SEQ ID NO 25
<211> LENGTH: 106
<212> TYPE: PRT
<213> ORGANISM: Artificial
<220> FEATURE:
<223> OTHER INFORMATION: Variable domain

<400> SEQUENCE: 25

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Pro Pro Lys Leu Leu Ile
            35                  40                  45

His Trp Ala Val Thr Arg Val Ser Gly Val Pro Asp Arg Phe Ser Gly
 50                  55                  60

Ser Gly Ser Gly Thr Asp Phe Thr Leu Thr Ile Ser Ser Leu Gln Ala
 65                  70                  75                  80

Glu Asp Val Ala Val Tyr Tyr Cys Gln Gln Tyr Ser Thr Tyr Pro Thr
                85                  90                  95

Phe Gly Gln Gly Thr Lys Leu Glu Ile Lys
            100                 105

<210> SEQ ID NO 26
<211> LENGTH: 125
<212> TYPE: PRT
<213> ORGANISM: Artificial
<220> FEATURE:
<223> OTHER INFORMATION: Variable domain

<400> SEQUENCE: 26

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
            20                  25                  30

Gly Ile Ser Trp Leu Arg Gln Ala Pro Gly Gln Gly Leu Glu Trp Met
            35                  40                  45

Gly Trp Val Asn Thr Asn Thr Gly Asn Pro Arg Tyr Ala Gln Gly Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95
```

```
Ala Arg Glu Gly Phe Ile Thr Thr Val Val Gly Ala Ala Gly Arg Phe
            100                 105                 110

Val Tyr Trp Gly Gln Gly Thr Leu Val Thr Val Ser Ser
        115                 120                 125

<210> SEQ ID NO 27
<211> LENGTH: 106
<212> TYPE: PRT
<213> ORGANISM: Artificial
<220> FEATURE:
<223> OTHER INFORMATION: Variable domain

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Thr Arg
            20                  25                  30

Leu Ala Trp Tyr Gln Gln Lys Pro Gly Gln Pro Pro Lys Leu Leu Ile
        35                  40                  45

Tyr Trp Ala Ser Thr Arg Gly Ser Gly Val Pro Asp Arg Phe Ser Gly
    50                  55                  60

Ser Gly Ser Gly Thr Asp Phe Thr Leu Thr Ile Ser Ser Leu Arg Ala
65                  70                  75                  80

Glu Asp Val Ala Val Tyr Tyr Cys Gln Gln Tyr Ser Thr Tyr Pro Thr
                85                  90                  95

Phe Gly Gln Gly Thr Lys Leu Glu Ile Lys
            100                 105

<210> SEQ ID NO 28
<211> LENGTH: 318
<212> TYPE: DNA
<213> ORGANISM: Artificial
<220> FEATURE:
<223> OTHER INFORMATION: NV115-3B VK Genart DNA sequence

<400> SEQUENCE: 28
gacatccaga tgacccagag ccccagcagc ctgagcgcct ctgtgggcga ccgggtgacc      60
atcacctgcc gggccagcca ggacatccac acccggctgg cctggtatca gcagaagccc     120
ggccagcccc ccaagctgct gatctactgg gccagcaccc gggccagcgg cgtgcccgac     180
cggtttagcg gcaccggcag cggcaccgac ttcaccctga ccatcagcag cctgcaggcc     240
gaggacgtgg ccgtgtacta ctgccagcag tacagcacct accccacctt cggccagggc     300
accaagcttg aaatcaaa                                                   318
```